United States Patent
Moore et al.

(10) Patent No.: US 6,245,020 B1
(45) Date of Patent: Jun. 12, 2001

(54) CATHETER ASSEMBLY WITH DISTAL END INDUCTIVE COUPLER AND EMBEDDED TRANSMISSION LINE

(75) Inventors: Thomas C. Moore, Fremont; Eric Williams, Fairfield; David A. White, San Jose; Donald S. Mamayek, Mountain View; Donald Masters, Sunnyvale; Martin Belef, San Jose; Veijo Soursa, Sunnyvale, all of CA (US)

(73) Assignee: SciMed Life System, Inc., Maple Grove, MN (US)

( * ) Notice: Subject to any disclaimer, the term of this patent is extended or adjusted under 35 U.S.C. 154(b) by 0 days.

(21) Appl. No.: 09/238,647

(22) Filed: Jan. 26, 1999

Related U.S. Application Data

(63) Continuation-in-part of application No. 09/013,463, filed on Jan. 26, 1998, now abandoned.

(51) Int. Cl.[7] ........................................................ A61B 8/12
(52) U.S. Cl. .............................................................. 600/466
(58) Field of Search .................................... 600/407, 424, 600/439, 459, 462–471; 607/122

(56) References Cited

U.S. PATENT DOCUMENTS

| | | | |
|---|---|---|---|
| 4,173,228 | * 11/1979 | Van Steenwyk et al. | 600/424 |
| 5,010,886 | * 4/1991 | Passafarn et al. | 600/463 |
| 5,295,484 | * 3/1994 | Marcus et al. | 600/439 |
| 5,588,432 | * 12/1996 | Crowley | 600/439 |
| 5,699,801 | * 12/1997 | Atalar et al. | 600/410 |
| 5,704,361 | * 1/1998 | Seward et al. | 600/459 |

* cited by examiner

Primary Examiner—Francis J. Jaworski
(74) Attorney, Agent, or Firm—Lyon & Lyon LLP

(57) ABSTRACT

A catheter assembly includes an elongate catheter body having a proximal end and a distal end with a drive cable disposed therein, the drive cable having a proximal end and a distal end, and rotatable relative to the catheter body. A first electro-magnetic element is disposed proximate the distal end of the catheter, and a second electro-magnetic element disposed proximate the distal end of the drive cable and in electrical communication with an operative element mounted at the end of the drive cable, the first and second electro-magnetic elements forming an inductive coupler. The catheter assembly can include various other distal operative elements, which are in communication with corresponding proximal operative elements via transmission lines embedded within the wall of the catheter body.

18 Claims, 12 Drawing Sheets

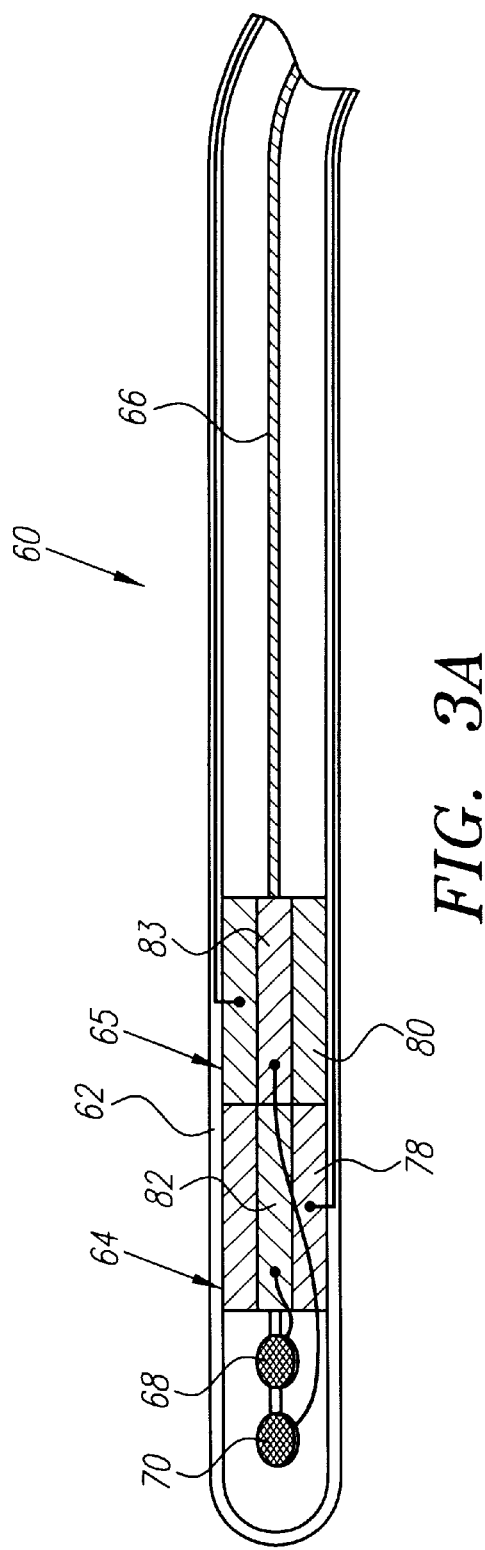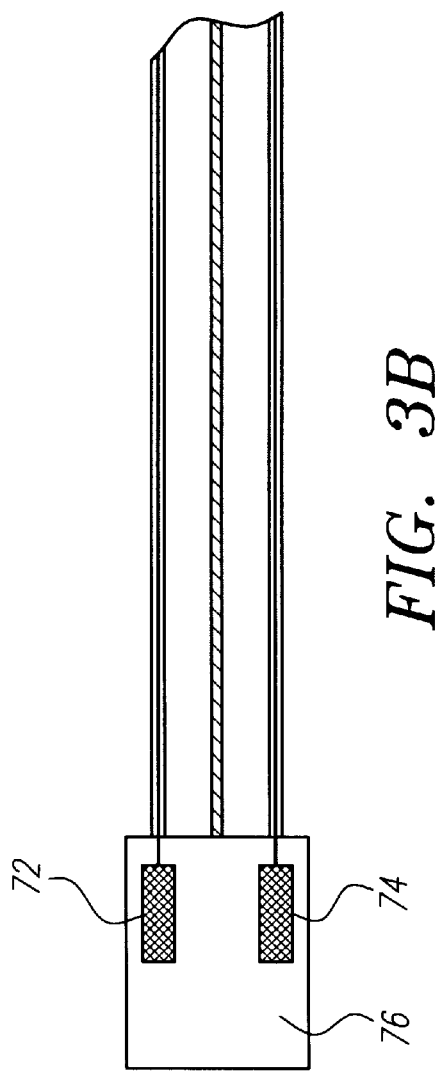
FIG. 3A
FIG. 3B

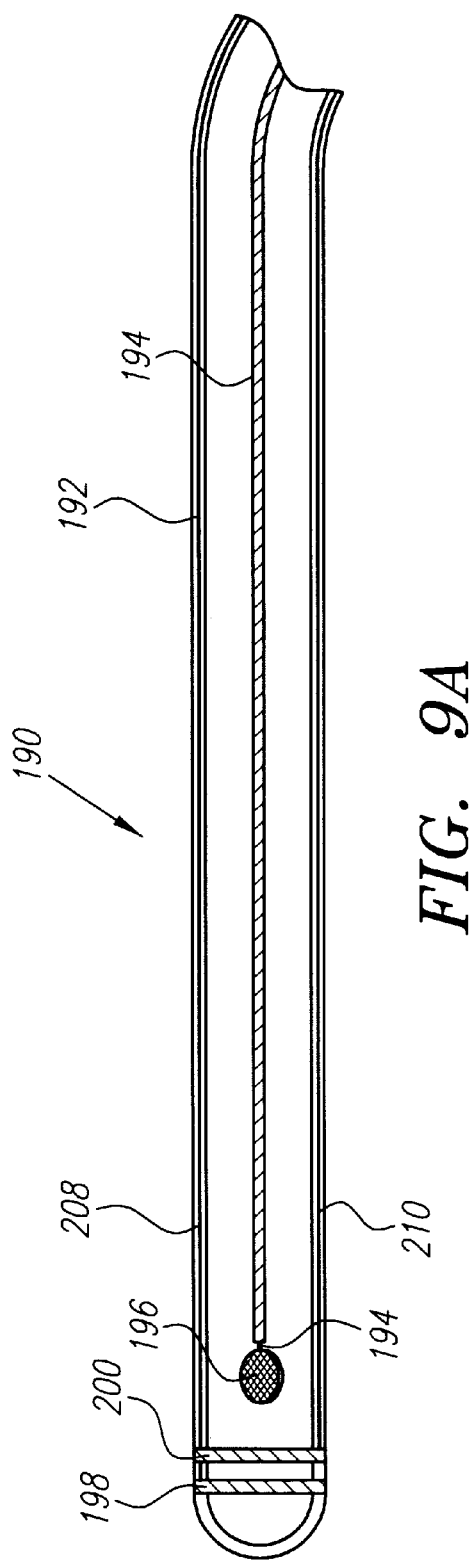
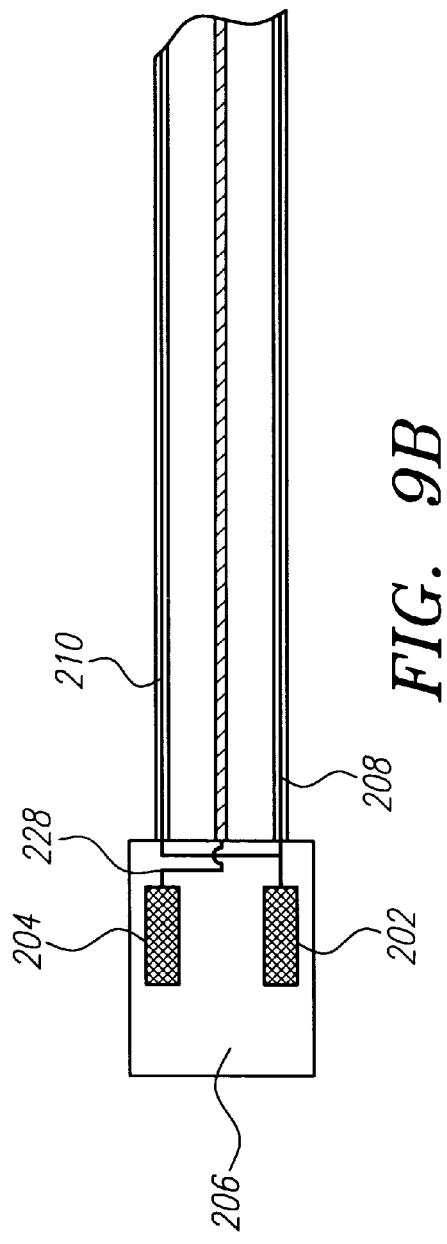

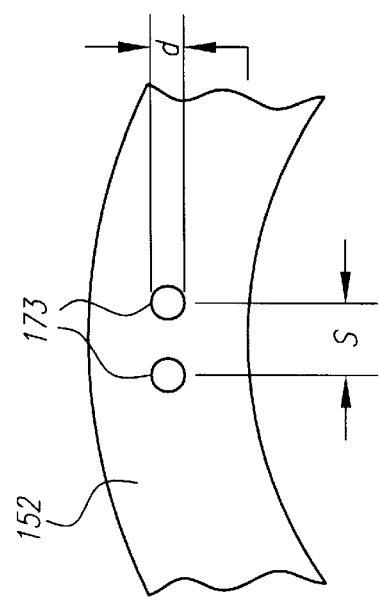
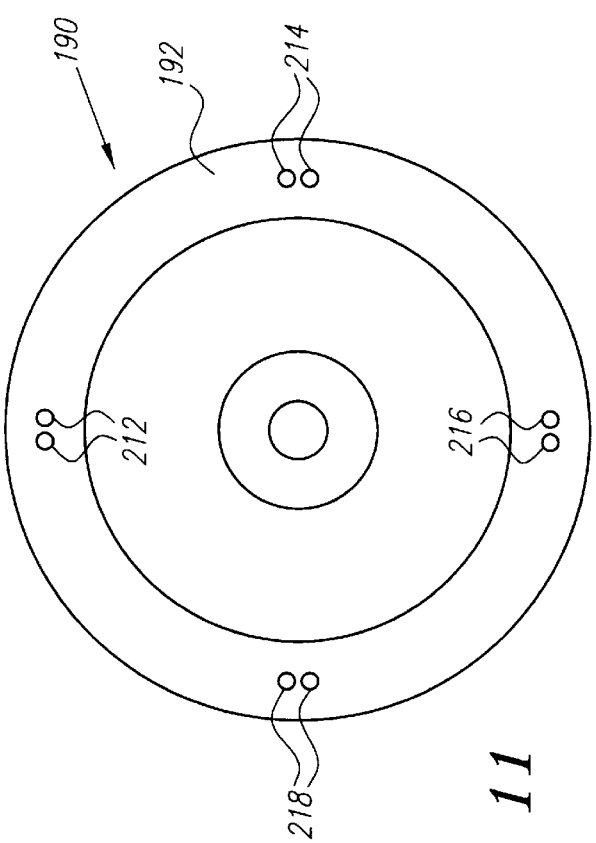
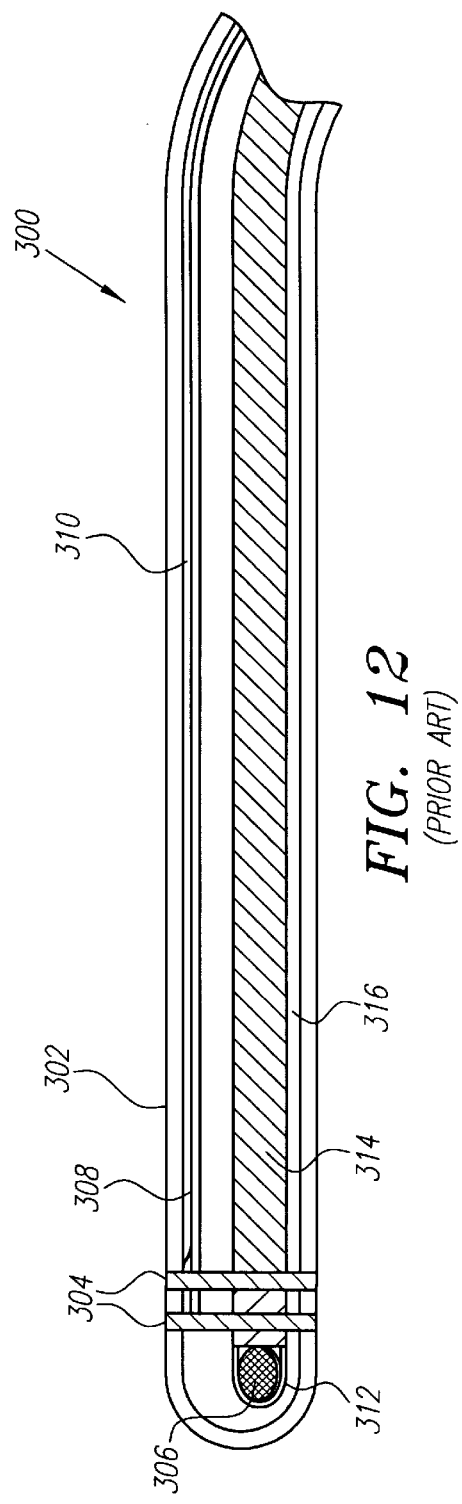
FIG. 13
FIG. 11
FIG. 12 (PRIOR ART)

CATHETER ASSEMBLY WITH DISTAL END INDUCTIVE COUPLER AND EMBEDDED TRANSMISSION LINE

This application is a C-I-P of Ser. No. 09/013,463 filed Jan. 26, 1998, ABN.

FIELD OF THE INVENTION

The present invention pertains to catheter systems and, more particularly, to intraluminal catheter assemblies used in diagnostic and therapeutic applications.

BACKGROUND

Intraluminal catheter assemblies are employed to diagnose and/or treat abnormalities within the human vasculature. A typical intraluminal catheter assembly includes a distally mounted operative element, such as, e.g., an ablation electrode, which is in electrical communication with a proximally located operative element, such as, e.g., an RF generator. Currently, intraluminal catheter assemblies include elongate catheter bodies in which internal lumens are extruded for the purpose of routing transmission lines between the distally mounted operative element and the proximally located operative element.

Often, intraluminal catheter assemblies support multiple distally mounted operative elements, thereby providing the physician with a single multi-functional platform. Because the radius of the catheter body must be small enough to be transported through the vasculature, however, the size and number of internal lumens which can be extruded through the catheter body becomes a critical factor, thereby limiting the amount, combination and/or performance of distally mounted operative elements supported by these catheter assemblies.

For example, as shown in FIG. 12, a typical ultrasonic imaging/ablation catheter assembly 300 includes an elongate catheter body 302 with distally mounted ablation electrodes 304 and a distally disposed rotatable ultrasonic transducer 306 to allow a physician to more easily image and ablate abnormal vasculature tissue.

The ablation electrodes 304 are electrically coupled to a proximally disposed RF generator (not shown) via transmission lines 308, which are routed through a first internal lumen 310 extruded within the catheter body 302. Operation of the RF generator transmits radio frequency electrical energy through the transmission lines 308 to the ablation electrodes 304, which in turn emit RF energy into the vasculature tissue adjacent the ablation electrodes 304.

The ultrasonic transducer 306 is mounted in a transducer housing 312 disposed within the catheter body 302. The ultrasonic transducer 306 is mechanically and rotatably coupled to a proximally disposed drive unit (not shown) via a drive cable 314 rotatably disposed within a second extruded internal lumen 316. The ultrasonic transducer 306 is electrically coupled to a proximally disposed signal transceiver (not shown) via a transmission line (not shown) disposed within the drive cable 314. Operation of the drive unit rotates the drive cable 314, and thus the ultrasonic transducer 306, with respect to the catheter body 302. Simultaneous operation of the transceiver alternately transmits and receives electrical energy to and from the ultrasonic transducer 306 via the drive cable disposed transmission line, thereby providing the physician with 360° imaging of the vasculature tissue adjacent the ultrasonic transducer 306.

The catheter assembly 300 is configured to allow the drive cable 314 and distally mounted ultrasonic transducer 306 to be "back loaded" (i.e., inserted or retracted) through the second interior lumen 316. The size of the ultrasonic transducer 306, and thus the integrity of the imaging data obtained therefrom, is thus limited by the size of the second interior lumen 316. The size of the second interior lumen 316, however, could be increased by eliminating the first interior lumen 308.

Another concern with respect to intraluminal catheter assemblies is the coupling of an electrical signal between a distal non-rotatable operative element and a proximal rotatable operative element, such as, e.g., the ultrasonic transducer 306 and transceiver employed in the catheter assembly 300 described above. Typically, to provide this inductive coupling, an inductive coupler is connected in parallel with the signal wires at the proximal end of the catheter. As such, that portion of the signal wires distal to the inductive coupler rotate with the transducer, and must therefore be installed within the entire length of the drive cable. Although a proximally disposed inductive coupler adequately provides inductive coupling between the transducer and the transceiver, this arrangement has several disadvantages.

For example, a signal wire disposed drive cable aggravates a phenomenon suffered by ultrasound imaging catheters called non-uniform rotational distortion ("NURD"). NURD is caused by frictional forces between the rotating imaging core and the inner wall of the catheter, which are magnified by the many twists and turns that a catheter must undergo so that the transducer can be positioned in the desired imaging location within the patient's body. These frictional forces cause the imaging core to rotate about its axis in a non-uniform manner, thereby resulting in a distorted image.

NURD can be minimized by "optimizing" the construction of the drive cable, for example, by varying the drive cable's diameter, weight, material, etc. The characteristics of the drive cable, however, are dictated in part by the signal wires disposed therein, thereby limiting this NURD-minimizing optimization. Further, the signal wires contribute non-uniformities to the drive cable that cannot be optimized.

A further disadvantage of a proximally disposed inductive coupler is that the diameter of the drive cable must be increased to accommodate the signal wires, thereby occupying space within the catheter that could otherwise be used to support other functions such as, e.g., pull-wire steerability, angioplasty balloon therapy, ablation therapy, or blood flow (Doppler) measurements.

A further disadvantage of a proximally disposed inductive coupler is that the remoteness of the coupler prevents usage thereof for transducer optimization, i.e., transducer tuning and matching or prevention of transducer low frequency mode emittance. Thus, additional measures must be employed to either optimize the transducer or to minimize the undesirable effects thereof.

For instance, at its normal frequency of operation, the transducer exhibits a net capacitive reactance. Thus, inductive reactance should be provided to "cancel" this capacitive reactance, so as to efficiently couple the transmit/receive signals to the transducer (e.g., to maximize signal-to-noise ratios). A proximally disposed inductive coupler does not provide the needed inductance, however, since the inductance producing structure must be placed along the signal wires in close proximity to the transducer. Instead, such a result can be accomplished by placing an inductive coil in series with the signal wires, as demonstrated in U.S. Pat. No. 4,899,757 issued to Pope, Jr. et al.

In addition to canceling the capacitive reactance produced by the transducer, it is also desirable to match the input impedance of the transducer with the characteristic impedance of the signal wires, so as to minimize signal reflection. In particular, a proximally disposed inductive coupler is by definition proximal to the signal wires and can therefore not be used to perform such matching. An attempt can be made to optimize the size and material of the transducer for matching of the signal wires therewith. Such optimization is limited, however, and to the extent any signal reflections are not eliminated, the signal power will accordingly be reduced.

Still further, an excited transducer naturally creates a low frequency mode of vibration that further produces multiples of higher frequency modes (e.g., 4 MHz, 8 MHz, 12 MHz, etc.). These unwanted signals cannot be eliminated through the use of a proximally disposed inductive coupler, but must be filtered out at the proximal end of the catheter. The signals within the frequency band in which the imaging system is to be operated cannot be filtered out, however, and must be dealt with as interference.

Theoretically, a parallel inductor can be placed in close proximity to the transducer to short out the low frequency mode, thereby eliminating the higher frequency modes. Such an arrangement, however, is complicated and expensive, and thus inefficient for the mere purpose of eliminating unwanted modes of transducer vibration.

Therefore, it would be desirable to increase the available space within a catheter body by eliminating or at least reducing the number of interior lumens that support transmission lines. It would be further desirable to improve the mechanical and electrical performance of a catheter that employs a distal rotatable operative element and a proximal non-rotatable operative element.

SUMMARY OF THE INVENTION

The present invention overcomes the afore-described drawbacks of conventional intraluminal catheter assemblies by providing improved intraluminal catheter assemblies that employ a distally disposed inductive coupling assembly and/or at least one conductor embedded in the exterior wall of an elongate catheter body to provide communication between respective distal and proximal operative elements.

In a first preferred embodiment, a catheter assembly according to the present invention includes an elongate catheter body having a proximal end and a distal end with a drive cable disposed therein and rotatable relative to the catheter body. A first electro-magnetic element is disposed proximate the distal end of the catheter body and in electrical communication with a proximal operative element proximate the proximal end of the catheter body. A second electro-magnetic element is rotatably coupled to the drive cable and in electrical communication with a distal operative element rotatably coupled to the drive cable. The first and second electro-magnetic elements form an inductive coupler.

In accordance with a further aspect of the present invention, the first electro-magnetic element comprises a stator fixably disposed in the catheter body, and the second electro-magnetic element comprises a rotor mounted to a distal end of the drive cable, wherein the stator comprises a generally hollow cylinder, and the rotor comprises a rod rotatably disposed in the hollow cylinder. The stator and rotor are preferably made of a ferrite material, with the stator having a first electrically conductive coil disposed on the inner surface of the hollow cylinder, and wherein the rotor having a second electrically conductive coil disposed on the outer surface of the rod.

The stator and rotor having opposing surface areas, wherein the respective stator and rotor surface areas, along with the respective diameter, size and number of turns of the first and second electrically conductive coils, are selected such that the value of the inductive reactance of the inductive coupler is substantially equal to the capacitive reactance of the operative element, which may be, e.g., an ultrasonic transducer.

In accordance with a still further aspect of the present invention, the catheter assembly includes a first conductor having a distal end electrically coupled to the stator and a proximal end configured for electrically coupling to a signal transceiver. Preferably, the first conductor is disposed within the catheter body, with the ratio of turns between the first and second electrically conductive coils being selected such that the input impedance looking into the inductive coupler from the transmission line substantially matches the characteristic impedance of the transmission line. The catheter assembly includes a second conductor having a proximal end electrically coupled to the rotor and a distal end electrically coupled to an ultrasonic transducer. The signal transceiver and ultrasonic transducer are configured to provide 360° imaging of body tissue, such as, e.g., arterial tissue.

In a second preferred embodiment, a catheter assembly according to the present invention includes an elongate catheter body having a proximal end and a distal end with a drive cable disposed therein and rotatable relative to the catheter body. First and second electro-magnetic elements are disposed proximate the distal end of the catheter body and respectively in electrical communication with first and second proximal operative elements proximate the proximal end of the catheter body. Third and fourth electro-magnetic elements are rotatably coupled to the drive cable and in electrical communication with first and second distal operative elements rotatably coupled to the drive cable. The first and third electro-magnetic elements form a first inductive coupler, and the second and fourth electro-magnetic elements form a second inductive coupler.

In accordance with a further aspect of the present invention, the first and second electro-magnetic elements respectively comprise first and second stators fixably disposed in the catheter body, and the third and fourth electro-magnetic elements comprise first and second rotors mounted to a distal end of the drive cable, wherein the stators respectively comprise generally hollow cylinders, and the rotors respectively comprise rods rotatably disposed in the hollow cylinders, respectively.

In accordance with a still further aspect of the present invention, the catheter assembly includes first and second conductors having distal ends electrically coupled to the first and second stators, respectively, and proximal ends configured for electrically coupling to first and second signal transceivers, respectively. The catheter assembly includes third and fourth conductors having proximal ends electrically coupled to the first and second rotors, respectively, and distal ends electrically coupled to first and second ultrasonic transducers, respectively. The first signal transceiver and first ultrasonic transducer are configured to provide 360° imaging of body tissue, such as, e.g., arterial tissue, and the second signal transceiver and second ultrasonic transducer are configured to provide Doppler measurements of the blood flow through a vessel, such as, e.g., an artery.

In a third preferred embodiment, a catheter assembly according to the present invention includes an elongate telescoping catheter body having a proximal end and a distal end with a drive cable disposed therein and rotatable relative to the catheter body. A first electro-magnetic element is disposed proximate the distal end of the catheter body and in electrical communication with a proximal operative element proximate the proximal end of the catheter body. A second electro-magnetic element is rotatably coupled to the drive cable and in electrical communication with a distal operative element rotatably coupled to the drive cable. The first and second electro-magnetic elements form an inductive coupler. The telescoping catheter body is movably disposed in a main catheter body to provide longitudinal displacement of the distal operative element relative to the main catheter body. The particular aspects of the third preferred embodiment are similar to those of the first preferred embodiment with the exception that the controlled longitudinal displacement of the telescoping catheter body relative to the main catheter body allows for longitudinally spaced 360° image slices.

In a fourth preferred embodiment, a catheter assembly according to the present invention includes an elongate catheter body with a first distal operative element disposed thereon. The first distal operative element is electrically coupled to a first proximal operative element via a transmission line embedded in the wall of the catheter body. The catheter assembly includes a drive cable and a second distal operative element rotatably coupled to the drive cable. The second distal operative element is electrically coupled to a second proximal operative element via a transmission line within the drive cable.

In accordance with a further aspect of the invention, the first distal operative element comprises a first ultrasonic transducer mounted to the distal end of the catheter body, such that the face of the ultrasonic transducer is perpendicular to the axis of the catheter body. The second distal operative element comprises a second ultrasonic transducer mounted to the distal end of the drive cable. The first and second proximal elements respectively comprise signal transceivers. The first signal transceiver and first ultrasonic transducer are configured to provide Doppler measurements of the blood flow through a vessel, such as, e.g., an artery, and the second signal transceiver and second ultrasonic transducer are configured to provide 360° imaging of body tissue, such as, e.g., arterial tissue. The catheter wall can be used as a portion of the transmission line.

In a fifth preferred embodiment, a catheter assembly according to the present invention includes an elongate catheter body with first and second distal operative elements disposed thereon. The first and second distal operative elements are electrically coupled to a first proximal operative element via respective first and second transmission lines embedded in the wall of the catheter body. The catheter assembly includes a drive cable and a third distal operative element rotatably coupled to the drive cable. The third distal operative element is electrically coupled to a second proximal operative element via a third transmission line within the drive cable.

In accordance with a further aspect of the invention, the first and second distal operative elements comprise respective first and second electrodes, such as, e.g., ablation electrodes, mounted to the distal end of the catheter body. The first proximal element comprises an RF generator. The third distal operative element comprises an ultrasonic transducer mounted to the distal end of the drive cable. The second proximal element comprises a signal transceiver. The first and second ablation elements and the RF generator are configured to provide ablation therapy to adjacent body tissue, such as, e.g., arterial tissue, and the ultrasonic transducer and signal transceiver are configured to provide 360° imaging of body tissue, such as, e.g., arterial tissue.

In a sixth preferred embodiment, a catheter assembly according to the present invention includes an elongate catheter body with a plurality of distal operative elements disposed thereon. The plurality of distal operative elements are respectively electrically coupled to at least one proximal operative element via a plurality of transmission lines embedded in the wall of the catheter body.

In accordance with a further aspect of the invention, the plurality of distal operative elements comprise respective transducer elements, which are circumferentially arranged around the catheter body to form a phased array. The proximal element comprises a transceiver, which is configured to provide phased electrical signals to the plurality of transducer elements.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which:

FIGS. 3A and 3B are cut-away, partial side views of a second preferred catheter assembly employing a distal inductive coupler;

FIGS. 9A and 9B are cut-away, partial side views of a fifth preferred catheter assembly employing two embedded transmission lines;

FIG. 11 is a cross-sectional view of the catheter assembly of FIGS. 9A and 9B employing four embedded transmission lines;

FIG. 12 is a cut-away, partial side view of a prior art catheter assembly employing an interior lumen disposed transmission line;

FIG. 13 is a cut-away, cross-sectional view of the guide sheath and transmission line of the catheter assembly of FIGS. 7A and 7B.

DETAILED DESCRIPTION OF THE INVENTION

Figure 1A:
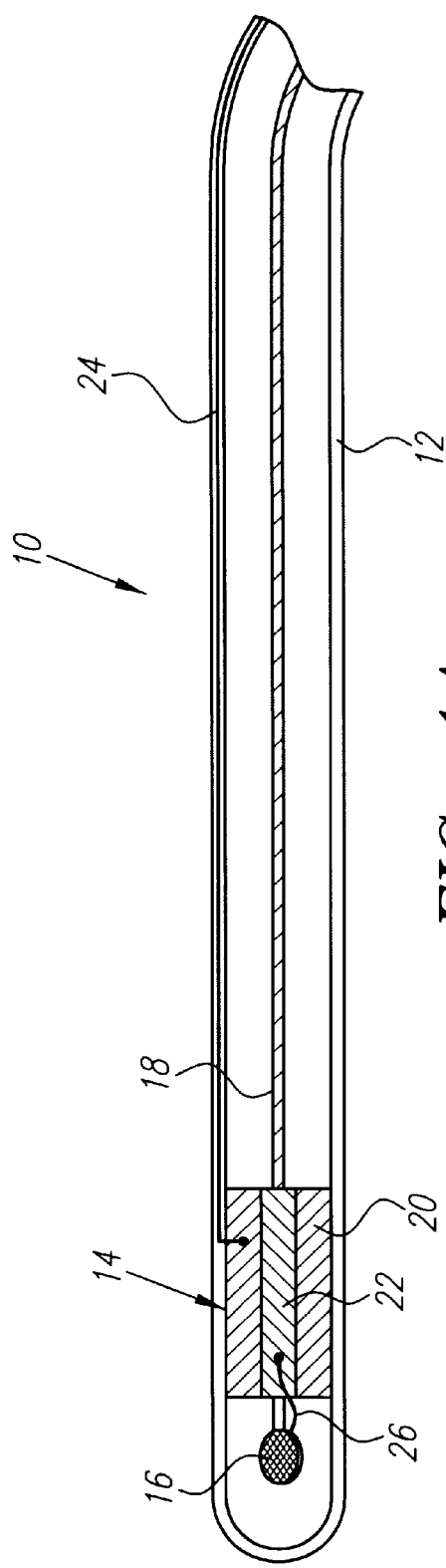
FIGS. 1A and 1B are cut-away, partial side views of a first preferred catheter assembly employing a distal inductive coupler.
Figure 1B:
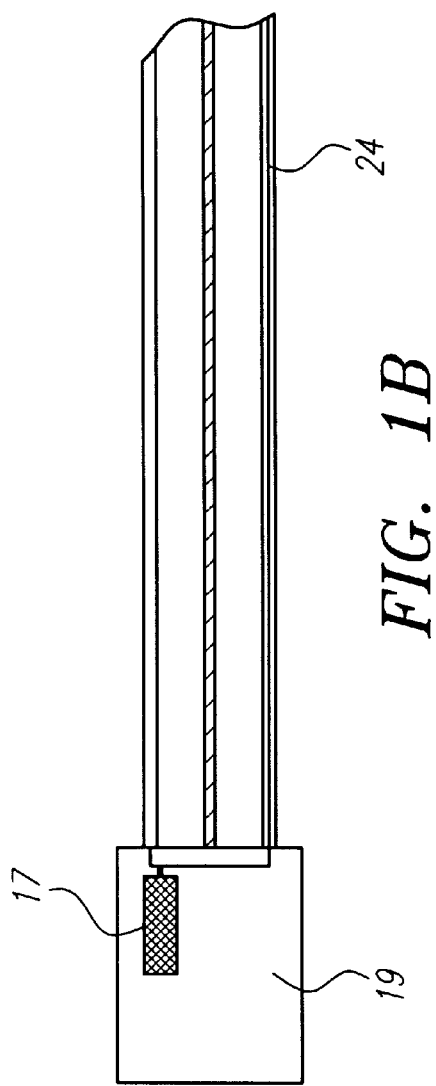
Figure 2:
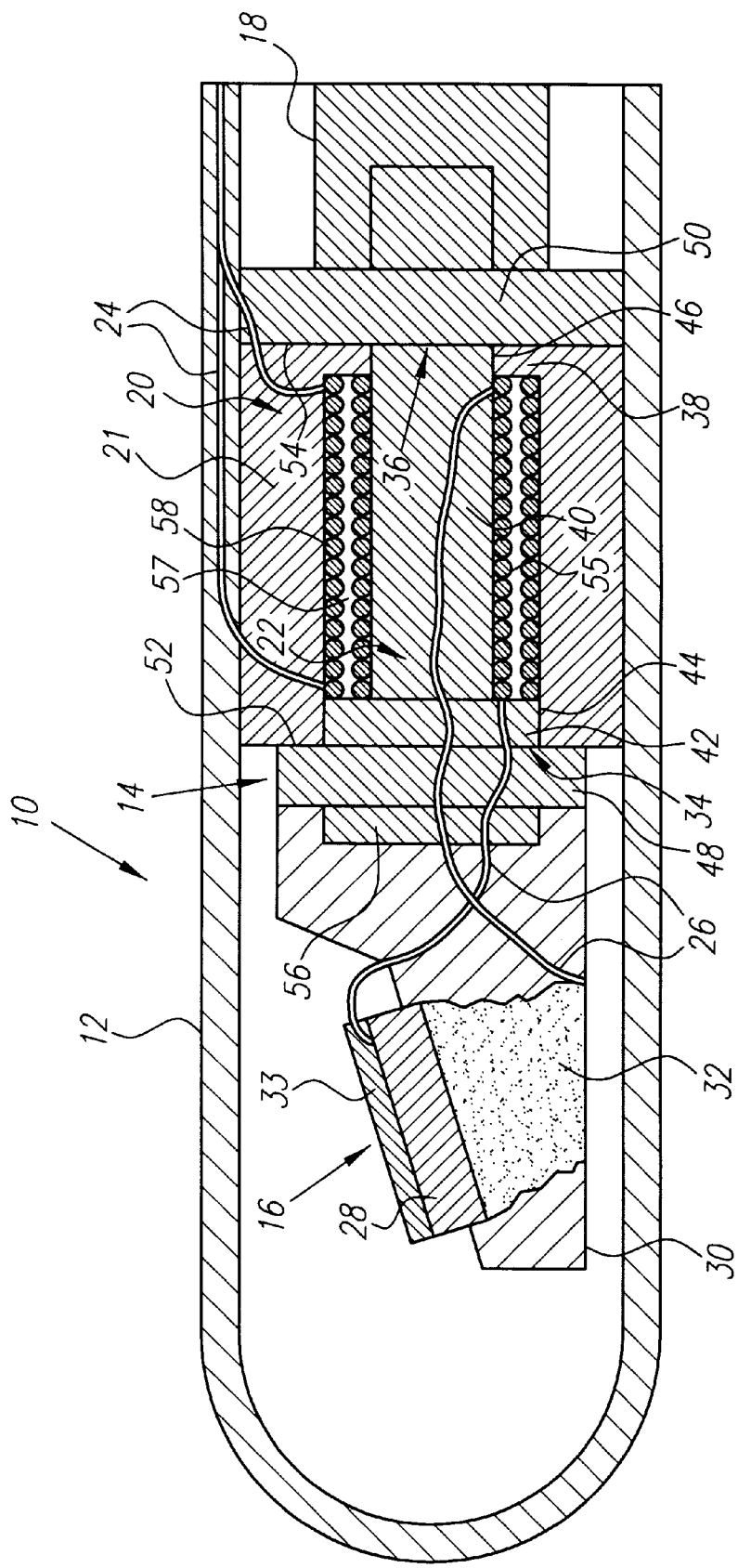
FIG. 2 is a cut-away, partial side view of the catheter assembly of FIGS. 1A and 1B.

Referring to FIGS. 1A, 1B and 2, a first exemplary catheter assembly 10 according to the present invention is provided for ultrasonic imaging of a patient's internal body tissue, e.g., the wall of an artery. The catheter assembly 10 generally includes an elongate catheter body 12, a distal inductive coupler 14, a drive cable 18, a rotatable distal operative element 16, and a non-rotatable proximal operative element 17. The drive cable 18 is disposed through substantially the entire catheter body 12, both of which are suitably mounted at the respective proximal ends thereof to a drive unit 19 proximal to the catheter assembly 10.

The inductive coupler 14 is disposed in the distal end of the catheter body 12 and generally includes a stator 20 and a rotor 22. The stator 20 is fixably mounted in the distal end of the catheter body 12. In particular, the stator 20 is supported by the inner surface of the catheter body 12, such as by way of heat shrinking the catheter body 12 over the stator 20. It can be appreciated, however, that other methods of fixing the stator 20 within the catheter body 12 can be accomplished by, e.g., embedding the stator 20 at least partially within the wall of the catheter body 12.

The rotor 22 is rotatably mounted inside the stator 20. In particular, the stator 20 includes a generally hollow cylinder 21 having a generally uniform inner diameter. The stator 20 includes an annular flange 38 integrally formed on the inner surface of the hollow cylinder 21 at the proximal end thereof. The stator 20 includes respective first and second apertures 34 and 36 through which the rotor 22 extends.

In particular, the distal end of the hollow cylinder 21 defines the first aperture 34, which has a diameter equal to the inner diameter of the hollow cylinder 21. The annular flange 38 defines the second aperture 36, which has a diameter smaller than that of the first aperture 34. The rotor 22 comprises a cylindrical rod 40 and a bearing disk 42 formed on and preferably integral with the distal end of the cylindrical rod 40. The diameters of the rod 40 and bearing disk 42 are substantially equal to the diameters of first aperture 34 and the second aperture 36, respectively, such that disposal of the rotor 22 in the stator 20 creates a first bearing surface 44 and a second bearing surface 46 therebetween.

In this manner, the respective first and second bearing surfaces 44 and 46 prevent lateral movement of the rotor 22 relative to the stator 20. The significance of the positional relationship of the rotor 22 and the stator 20 is the close proximity therebetween, such that the inductive efficiency between the stator 20 and the rotor 22 is maximized.

That is, an alternating electrical current applied to either the stator 20 or the rotor 22 creates a corresponding alternating electrical current on the other when the rotor 22 rotates relative to the stator 20. Thus, the rotor 22 and stator 20 can also, e.g., comprise rotatable and non-rotatable disks, respectively, that face one another.

The rotor 22 includes a thrust disk 48 and a thrust washer 50. The thrust disk 48 is formed on and preferably integral with the distal end of the rod 40. The thrust washer 50 is disposed about and fixed to the proximal end of the rod 40. The thrust disk 48 and thrust washer 50 cooperate to form a first thrust surface 52 and a second thrust surface 54.

More particularly, the thrust disk 48 has a diameter greater than that of the first aperture 34 and is distally adjacent to the stator 20, such that the proximal surface of the thrust disk 48 is in contact with the distal surface of the stator 20. The thrust washer 50 has a diameter greater than that of the second aperture 36 and is proximally adjacent to the stator 20, such that the distal surface of the thrust washer 50 is in contact with the proximal surface of the stator 20. In this manner, the respective first and second thrust surfaces 52 and 54 prevent longitudinal movement of the rotor 22 relative to the stator 20.

The distal operative element 16 comprises an ultrasonic transducer element 28 fixably mounted to a conductive housing 30, such that the face of the transducer element 28 is substantially parallel to the axis of the elongate catheter body 12. In preferred embodiments, there is a slight angle between the face of the transducer element 28 and the axis of the catheter assembly 10, thereby resulting in a "conical sweep" during imaging.

The proximal element 17 comprises a transceiver for alternately transmitting and receiving electrical signals to and from the transducer element 28 to obtain data for imaging the walls of the vessel in which the catheter assembly 10 is disposed. It can be appreciated, however, that the distal operative element 16 and the proximal operative element 17 are not limited to a transducer element 28 and a transceiver, respectively, but can, without straying from the principles taught by this invention, respectively comprise any rotatable and non-rotatable device that are in electrical communication with one another.

A conductive transducer backing material 32 made of a suitable material is potted in the housing 30 and beneath the transducer element 28, such that substantially all of the ultrasonic energy emitted by the transducer element 28 into the transducer backing material 32 is attenuated therein.

Conversely, a transducer matching material made of a suitable material is bonded to the face of the transducer element 28 as a transducer matching layer 33 opposite the transducer backing material 32. The purpose of the matching layer, or multiple matching layers, 33 is to improve transducer efficiency by maximizing the propagation of energy through the matching layer(s) and enhance the signal bandwidth. The transceiver 17 is mounted within the drive unit 19. The transceiver 17 can, however, be mounted to any stationary platform that is proximal to the inductive coupler 14 without straying from the principles taught by this invention The housing 30, the rotor 22, and the drive cable 18 are mechanically and rotatably coupled to the drive unit 19, so that they rotate as an integral unit relative to the stator 20 when the drive unit 19 is operated. In particular, the proximal end of the drive cable 18 is suitably mounted to the drive unit 19 using means known in the art. The drive cable 18 is preferably designed such that it possesses a high torsional stiffness and a low bending stiffness.

For example, the drive cable 18 can be made of two counterwound layers of multifilar coils that are fabricated using techniques disclosed in Crowley et al., U.S. Pat. No. 4,951,677, and fully incorporated herein by reference. The proximal end of the rod 40 is suitably mounted to the inside of the drive cable 18 using known means such as welding. The rotor 22 includes a housing mounting disk 56 formed on and preferably integral with the proximal end of the rod 40. The housing mounting disk 56 is distal to the bearing disk 48, and is suitably mounted to the inside of the housing 30 using known means such as welding.

The transceiver 17 is electrically coupled to the transducer element 28 through the inductive coupler 14 and respective first and second transmission lines 24 and 26. In particular, the transceiver 17 is electrically coupled to the stator 20 via the first transmission line 24. The first transmission line 24 is preferably twisted pair, but can be any electrical conductor used in the manufacture of catheters, such as, e.g., coaxial cable. The first transmission line 24 is fixed relative to the stator 20 and is preferably disposed within the catheter body 12 using known extrusion methods, such as that disclosed in Woinowski, U.S. Pat. No. 4,277,432, and fully incorporated herein by reference. However, the first transmission line 24 can alternatively be disposed within a catheter lumen using means known in the art.

The transducer element 28 is electrically coupled to the rotor 22 of the inductive coupler 14 via the second transmission line 26. Again, the second transmission line 26 is preferably made of twisted pair, but can also be made of coaxial cable. The second transmission line 26 is suitably bonded to the rotor 22 and housing 30, such that the second transmission line 26 integrally rotates with the housing 30, rotor 22, and drive cable 18.

As mentioned above, the stator 20 and the rotor 22 are inductively coupled. In particular, the inductive coupler 14 includes an annular space 57 formed between the inner surface of the cylinder 21 and the outer surface of the rod 40. The stator 20 includes a first electrically conductive coil 58 disposed in the annular space 57 and suitably bonded to the inner surface of the cylinder 21. The rotor 22 includes a second electrically conductive coil 55 disposed in the annular space 57 and suitably bonded to the outer surface of the rod 40. The annular space 57 allows a close positional relationship between the respective first and second coils 58 and 55 without any contact therebetween.

The first transmission line 24 is connected to each end of the coil 58, and the second transmission line 26 is connected to each end of the second coil 55. In this manner, the transceiver 17 and the transducer element 28 are electrically connected in parallel to the stator 20 and the rotor 22, respectively.

To maximize the inductive efficiency of the inductive coupler 14, the stator 20 and the rotor 22 are preferably made of a magnetic material such as ferrite, and the respective first and second coils 58 and 55 are preferably made of copper. The particular characteristic impedance of the inductive coupler 14 are preferably chosen so as to tune the signal carrying capability of the first transmission line 24.

That is, the wire diameter, size, and number of turns of the respective first and second coils 58 and 55 and the surface area of the stator 20 and the rotor 22 are chosen, such that the inductive coupler 14 exhibits an inductive reactance which is substantially equivalent to the net capacitive reactance of the transducer element 28 at the operating frequency thereof. Also, to prevent signal reflections between the second transmission line 26 and the inductive coupler 14, the ratio of turns between the respective first and second coils 58 and 55 preferably should be chosen, such that the input impedance looking into the inductive coupler 14 matches the characteristic impedance of the first transmission line 24.

In use, the catheter assembly 10 is intravascularly inserted into a patient. For example, if the catheter assembly 10 is to be used so as to image a patient's coronary arteries, then it may conveniently be inserted percutaneously into the patient's femoral artery. The catheter assembly 10 is then maneuvered by the physician until a desired region of the patient's coronary arteries is adjacent the transducer element 28.

With the catheter assembly 10 properly positioned, ultrasonic imaging of the adjacent arterial tissue may be accomplished conventionally by transmitting electrical pulses to and receiving electrical pulses from the rotating transducer element 28.

In particular, the drive unit 19 is operated to rotate the transducer element 28 at a high rotational speed. In particular, the drive unit 19 provides rotational energy to the drive cable 18, which in turn provides rotational energy to the transducer element 28 via the rotor 22 of the inductive coupler 14. Prevention of any lateral and longitudinal movement of the rotor 22 with respect to the stator 20 via the bearing surfaces 44 and 46 and the thrust surfaces 52 and 54, respectively, allows a uniform inductive relationship between the stator 20 and the rotor 22.

The transceiver 17 transmits an electrical pulse to the stator 22 via the first transmission line 24, thereby charging the first coil 58. The charge on coil 58 is inductively coupled to the coil 55. The inductive coupling is maximized by the close positional relationship between the stator 20 and the rotor 22 at the respective first and second bearing surfaces 44 and 46. The inductive charge on the second coil 55 is then transmitted to the transducer element 28 via the second transmission line 26.

The electrically excited transducer element 28 emits ultrasonic energy, which reflects off of the arterial wall of the patient and back into the transducer element 28. This reflected ultrasonic energy produces a return electrical signal in the transducer element 28, which is transmitted back to the rotor 22 via the second transmission line 26, thereby charging the second coil 55. The charge on the coil 55 is inductively coupled to the coil 58. The inductive charge on the first coil 58 is then transmitted back to the transceiver 17 via the first transmission line 24. This return electrical signal is further processed as imaging data. The transceiver 17 alternately transmits electrical pulses to and receives return electrical signals from the transducer element 28 to obtain further imaging data.

Since the inductive coupler 14 is located closely adjacent the transducer element 28, an effectively increased signal to noise ratio results with the benefit being that higher quality imaging signals are transmitted into the transceiver 17. That is, since the inductive reactance of the inductive coupler 14 is equivalent to the net capacitive reactance of the transducer element 28, the reactive power of the return electrical pulse is minimized.

Further, since the inductive coupler 14 is used to match the impedance of the transducer element 28 to the characteristic impedance of the first transmission line 24, signal reflections are minimized. Lastly, since the inductive coupler 14 is electrically connected in parallel to the transducer element 28, the inductive coupler 14 shorts out any low frequency modes of vibration produced by the transducer element 28, thus preventing non-filterable higher frequency modes from being further produced. As such, the signal to noise ratio of the return electrical signal is increased, thus resulting in higher quality imaging.

Figure 4:
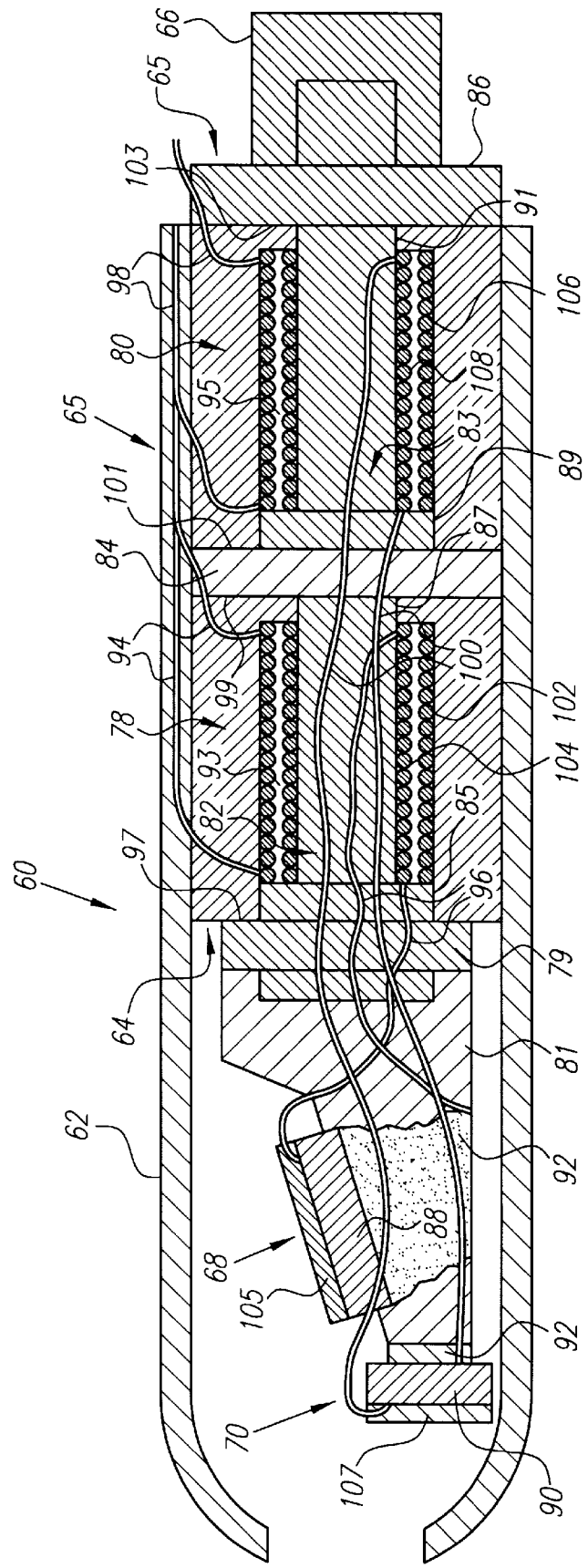
FIG. 4 is a cut-away, partial side view of the catheter assembly of FIGS. 3A and 3B.

Referring to FIGS. 3A, 3B and 4, a second exemplary catheter assembly 60 is provided for measuring the velocity of the blood within a patient's vessel, while also providing ultrasonic imaging of the vessel wall. The catheter assembly 60 generally includes an elongate catheter body 62, respective first and second distal inductive couplers 64 and 65, a drive cable 66, respective first and second rotatable distal operative elements 68 and 70, and respective first and second non-rotatable proximal operative elements 72 and 74.

The drive cable 66 is disposed through substantially the entire catheter body 62, both of which are mounted at the respective proximal ends thereof to a drive unit 76 proximal to the catheter assembly 60. The respective first and second inductive couplers 64 and 65 are disposed in the distal end of the catheter body 62 and generally include a first stator 78 and first rotor 82, and a second stator 80 and second rotor 83, respectively. The respective first and second inductive couplers 64 and 65 are in a coaxial relationship with each other.

In particular, the respective first and second stators 78 and 80 are supported by the inner surface of the catheter body 62, such as by way of heat shrinking the catheter body 62 thereover. It can be appreciated, however, that other methods of fixing the respective first and second stators 78 and 80 within the catheter body 62 can be accomplished by, e.g., embedding the respective first and second stators 78 and 80 at least partially within the wall of the catheter body 62.

The structures of the respective first and second inductive couplers 64 and 65 are similar to the structure described above with respect to the inductive coupler 14 of the catheter assembly 10, with the exception that the first rotor 82 lacks a thrust washer and the second rotor 83 lacks a housing mounting disk and a thrust disk. The first stator 78 and the first rotor 82 form first and second bearing surfaces 85 and 87 and a first annular space 93 therebetween, and the second stator 80 and the second rotor 83 form third and fourth bearing surfaces 89 and 91 and a second annular space 95 therebetween.

The catheter assembly 60 includes an isolation disk 84 disposed between the respective first and second inductive couplers 64 and 65. The isolation disk 84 is made of an electrical insulative material to prevent electrical conduction between the respective first and second inductive couplers 64 and 65.

In particular, the proximal end of the first stator 78 and the distal end of the second stator 80 respectively abut the distal and proximal faces of the isolation disk 84. The proximal end of the first rotor 82 and the distal end of the second rotor 83 are fixably mounted to the distal and proximal faces of the isolation disk 84, respectively. Preferably, the faces of the isolation disk 84 have recesses formed therein to receive the respective ends of the rotors 82 and 83.

The second rotor 83 includes a thrust washer 86 disposed about and fixed to the proximal end of the rod rotor 83. A thrust disk 79 formed at the distal end of the first rotor 82, the thrust washer 86, and the isolation disk 84 cooperate to form respective first, second, third, and fourth thrust surfaces 97, 99, 101 and 103 in much the same manner as that described above with reference to the inductive coupler 22 of the catheter assembly 10.

In this manner, the inductive efficiency of the respective first and second inductive couplers 64 and 65 is increased. In particular, the bearing surfaces 85, 87, 89, and 91 and thrust surfaces 97, 99, 101, and 103 provide a close positional relationship and prevent lateral and longitudinal movement between the stators 78 and 80 and rotors 82 and 83, respectively.

The first distal operative element 68 comprises a first ultrasonic transducer 88 fixably mounted to a conductive housing 81, such that the face of the first ultrasonic transducer element 88 is substantially parallel to the axis of the elongate catheter body 62.

In preferred embodiments, there is a slight angle between the face of the first ultrasonic transducer element 88 and the axis of the catheter assembly 60, thereby resulting in a "conical sweep" during imaging. The first proximal element 72 comprises a first transceiver for alternately transmitting and receiving electrical signals to and from the first transducer element 88 to obtain data for imaging the walls of the vessel in which the catheter assembly 60 is disposed.

The second distal operative element 70 comprises a second ultrasonic transducer element 90 fixably mounted to the distal end of the conductive housing 81, such that the face of the second transducer element 90 is substantially perpendicular to the axis of the elongate catheter body 62.

The second proximal element 74 comprises a second transceiver for alternately transmitting and receiving electrical signals to and from the second transducer element 90 to obtain data for Doppler measurements of the blood flow within the vessel in which the catheter assembly 60 is disposed. It can be appreciated, however, that the distal operative elements 68 and 70 and proximal operative elements 72 and 74 are not respectively limited to the transducer elements 88 and 90 and the transceivers, but can, without straying from the principles taught by this invention, respectively comprise any rotatable and non-rotatable devices that are in electrical communication with one another.

A conductive transducer backing material 92 made of a suitable material is potted in the housing 81, such that substantially all of the ultrasonic energy emitted by the transducer elements 88 and 90 into the transducer backing material 92 is attenuated therein.

Conversely, transducer matching material made of a suitable material is formed onto the faces of the respective transducer elements 88 and 90 as respective transducer matching layers 105 and 107 opposite the transducer backing material 92. The purpose of the matching layer 105 and 107, or multiple matching layers, is to improve transducer efficiency by maximizing the propagation of energy through the matching layer(s), and enhance the signal bandwidth. The respective transceivers 72 and 74 are mounted within the drive unit 76, but can, however, be mounted to any stationary platform that is proximal to the inductive coupler 64 without straying from the principals taught by this invention.

The rotors 82 and 83 are mechanically and rotatably mounted to the housing 81 and the drive cable 66, respectively, in much the same manner as that described above with reference to the rotor 22, housing 30, and drive cable 18. Thus, the housing 81, the respective first and second rotors 82 and 83, and the drive cable 66 rotate as a single unit.

The first transceiver 72 is electrically coupled to the first transducer element 88 through the first inductive coupler 64 and respective first and second transmission lines 94 and 96, and the second transceiver 74 is electrically coupled to the second transducer element 90 through the second inductive coupler 65 and respective third and fourth transmission lines 98 and 100 in much the same manner as described above with respect to the transceiver 17 and the transducer element 28 of the catheter assembly 10.

In particular, the transceivers 72 and 74 are respectively electrically coupled to the stators 78 and 80, via respective first and third transmission lines 94 and 98. The transmission lines 94 and 98 are preferably twisted pair, but can be any electrical conductor used in the manufacture of catheters, such as, e.g., coaxial cable. The first and third transmission lines 94 and 98 are respectively fixed relative to the stators 78 and 80, and are preferably disposed within the catheter body 62 using known extrusion methods. The transmission lines 94 and 98, however, can also be disposed within a catheter lumen (not shown) using means known in the art.

The transducer elements 88 and 90 are respectively electrically coupled to the rotors 82 and 83, via respective second and fourth transmission lines 96 and 100. Again, the transmission lines 96 and 100 are preferably made of twisted pair, but can also be made of coaxial cable. The second transmission line 96 is suitably bonded to the first rotor 82 and the housing 81, and the fourth transmission line 100 is suitably bonded to the second rotor 83 and the housing 81, such that the transmission lines 96 and 100 integrally rotate with the housing 81, the rotors 82 and 83, and the drive cable 66.

As mentioned above, the stators 78 and 80 are inductively coupled to the rotors 82 and 83, respectively. In particular, the first stator 78 and the second stator 80 respectively include a first electrically conductive coil 102 and a third electrically conductive coil 106 suitably bonded to the inner surfaces thereof, and the first rotor 82 and the second rotor 83 include a second electrically conductive coil 104 and a fourth electrically conductive coil 108 suitably bonded to the outer surfaces thereof.

The first annular space 93 formed between the first stator 78 and the first rotor 82, and the second annular space 95 formed between the second stator 80 and the second rotor 83 allow a close positional relationship between the respective first and second coils 102 and 104 and between the respective third and fourth coils 104 and 108, without any contact therebetween. The respective first, second, third, and fourth transmission lines 94, 96, 98, and 100 are connected to the ends of the respective first, second, third, and fourth coils 102, 104, 106, and 108, respectively, as shown.

In this manner, the respective first and second transceivers are electrically connected in parallel to the respective first and second stators 78 and 80, respectively, and the respective first and second transducer elements 88 and 90 are electrically connected in parallel to the respective first and second rotors 82 and 83, respectively.

As with the inductive coupler 14 of the catheter assembly 10, the various parameters of the respective first and second inductive couplers 64 and 65 can be chosen to maximize the efficiency of the catheter assembly 60.

In use, the catheter assembly 60 is intravascularly inserted into a patient in much the same manner as that described above with reference to the catheter assembly 10. With the catheter assembly 60 properly positioned, ultrasonic imaging of the adjacent arterial tissue may be accomplished conventionally with the first transducer element 88 in much the same manner as that described above with respect to the catheter assembly 10.

In addition, catheter assembly 60 can be employed to provide Doppler data on the blood velocity within the blood vessel by transmitting electrical pulses to and receiving electrical signals from the second transducer element 90.

In particular, the second transceiver transmits an electrical signal to the second stator 80 via the third transmission line 98, thereby charging the third coil 106. The charge on the third coil 106 is inductively coupled to the fourth coil 108. This inductive coupling is maximized by the close positional relationship between the second stator 80 and the second rotor 83 at the respective third and fourth bearing surfaces 89 and 91. The inductive charge on the fourth coil 108 is then transmitted to the second transducer element 90 via the fourth transmission line 100.

The electrically excited second transducer element 90 emits ultrasonic energy, which reflects off of the blood flowing in the vessel and back into the second transducer element 90. This reflected ultrasonic energy produces a return electrical signal in the second transducer element 90, which is transmitted back to the second rotor 83 via the fourth transmission line 100, thereby charging the fourth coil 108. The charge on the fourth coil 108 is inductively coupled to the third coil 106.

The inductive charge on the third coil 106 is then transmitted back to the second transceiver via the third transmission line 98. This return electrical pulse is further processed as Doppler data. The second transceiver alternately transmits electrical pulses to and receives return electrical signals from the second transducer element 90 to obtain further Doppler data.

The benefits and advantages obtained by disposing the respective first and second inductive couplers 64 and 65 in the distal end of catheter assembly 60 adjacent to the respective first and second transducer elements 88 and 90 are the same as described above with respect to catheter assembly 10.

Figure 5A:
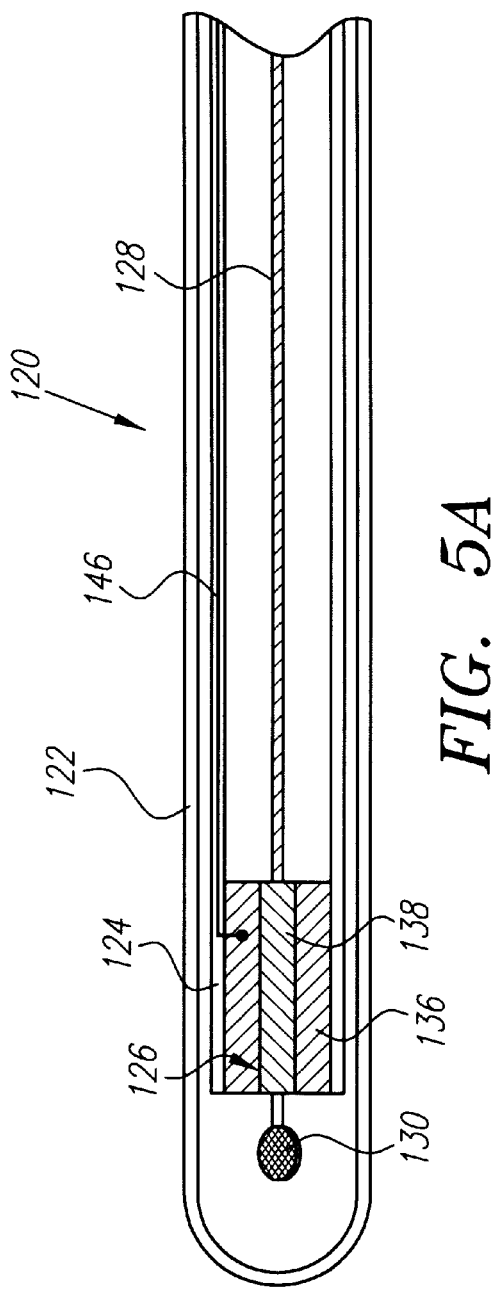
FIGS. 5A and 5B are cut-away, partial side views of a third preferred catheter assembly employing a distal inductive coupler.
Figure 5B:
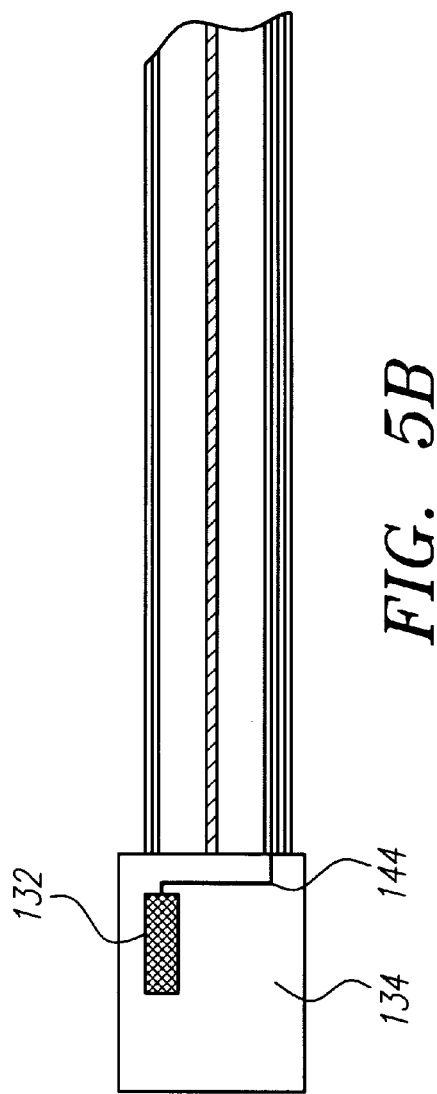
Figure 6:
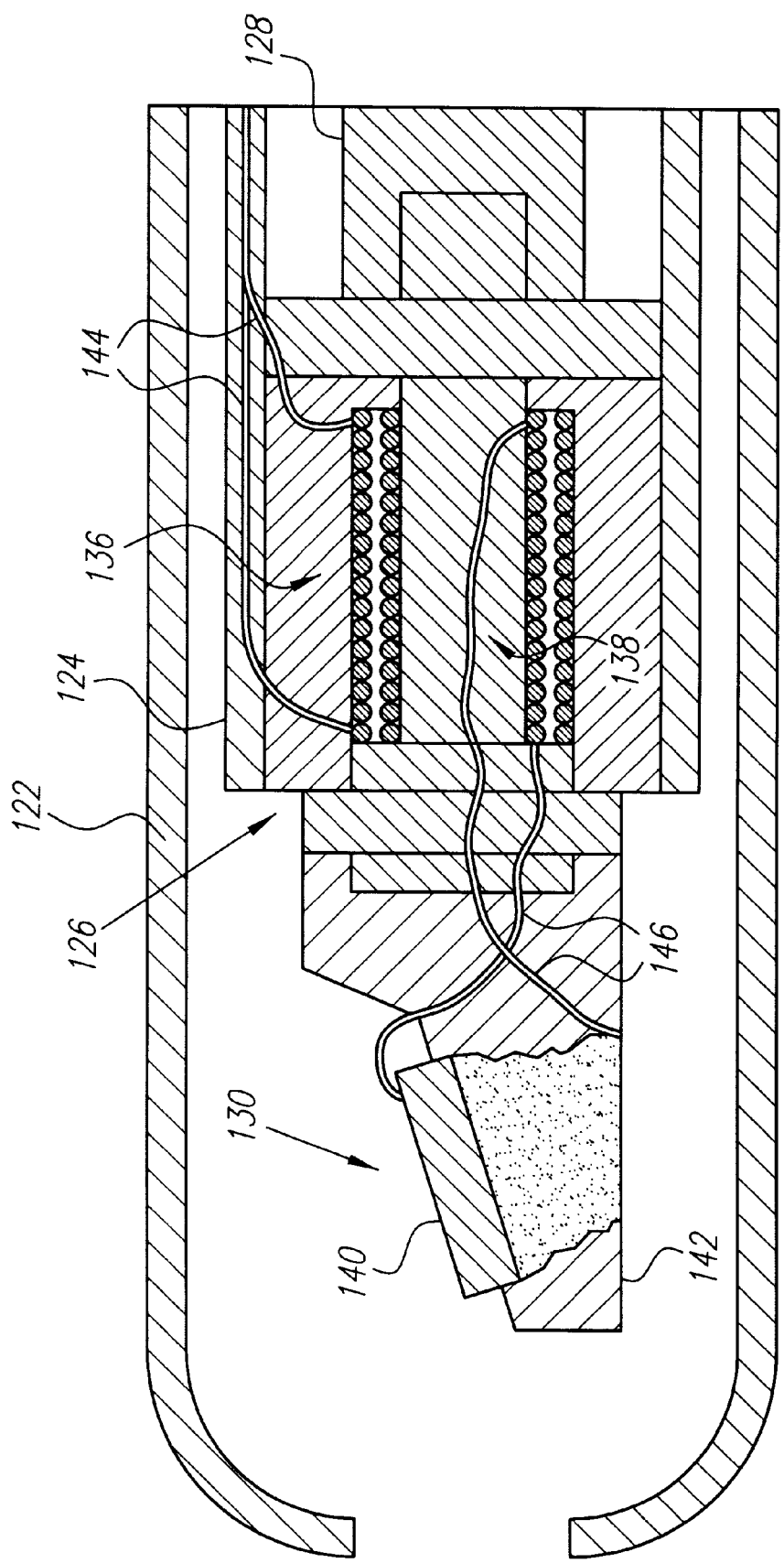
FIG. 6 is a cut-away, partial side view of the catheter assembly of FIGS. 5A and 5B.

Referring to FIGS. 5A, 5B, and 6, a third exemplary catheter assembly 120 generally includes a main elongate catheter body 122, a telescoping elongate catheter body 124, a distal inductive coupler 126, a drive cable 128, a rotatable distal operative element 130, and a non-rotatable proximal operative element 132. The telescoping catheter body 124 is movably disposed in the main catheter body 122. The drive cable 128 is disposed through substantially the entire telescoping catheter body 124. The drive cable 128, the main catheter body 122, and the telescoping catheter body 124 are mounted at the respective proximal ends thereof to a drive unit 134 proximal to the catheter assembly 120. The drive unit 134 can be any drive unit that is suitable for use with a telescoping catheter, of which many are known in the art.

The inductive coupler 126 is disposed in the distal end of the telescoping catheter body 124 and generally includes a stator 136 and a rotor 138. The distal operative element 130 is disposed in the main catheter body 122 distal to the telescoping catheter body 124. The operative element 130 can, however, be partially or fully disposed in the distal end of the telescoping catheter body 124.

In particular, the structure and positional relationship between the stator 136 and the rotor 138 of the inductive coupler 126 is similar to that described above with respect to the stator 20 and the rotor 22 of the inductive coupler 14 of catheter assembly 10. The distal operative element 130 comprises an ultrasonic transducer 140 with transducer matching and backing layers (not shown) fixably mounted to a conductive housing 142 in much the same manner as described above with respect to the transducer 28 and the housing 30 of the catheter assembly 10.

The proximal element 132 comprises a transceiver for alternately transmitting and receiving electrical signals to and from the transducer 140 to obtain data for imaging the walls of the vessel in which the catheter assembly 120 is disposed. It can be appreciated, however, that the distal operative element 130 and the proximal operative element 132 are not limited to the transducer 140 and the transceiver, respectively, but can, without straying from the principles taught by this invention, respectively comprise any rotatable and non-rotatable device that are in electrical communication with one another.

The transceiver 132 is mounted within the drive unit 134. The transceiver 132 can, however, be mounted to any stationary platform that is proximal to the inductive coupler 126 without straying from the principles taught by this invention.

The housing 142, the rotor 138, and the drive cable 128 are mechanically and rotatably coupled to the drive unit 134 in much the same manner as described above with respect to the housing 30, the rotor 22, the drive cable 18, and the drive unit 19 of catheter assembly 10. Likewise, the transceiver 132 is electrically coupled to the transducer 140 through the inductive coupler 126 and respective transmission lines 144 and 146 in much the same manner as described above with respect to the transceiver 17 and the transducer element 28 of catheter assembly 10, with the exception that the first transmission line 144 is disposed in the telescoping catheter body 124.

In use, the catheter assembly 120 is intravascularly inserted into a patient in much the same manner as that described above with reference to catheter assembly 10. With the catheter assembly 120 properly positioned, ultrasonic imaging of the adjacent arterial tissue may be accomplished conventionally with the transducer element 140 in much the same manner as that described above with respect to catheter assembly 10.

In addition, by manually operating the drive unit 134, the telescoping catheter body 124 can be moved longitudinally relative to the main catheter body 122 to place the transducer 140 adjacent to various desired imaging locations within the patient's vessel. Further, by automatically operating the drive unit 134, the telescoping catheter body 124 can be moved longitudinally relative to the main catheter body 122 in a controlled and uniform manner to data samples representing longitudinally spaced-apart 360 "slices" of the patient's interior vessel walls, which can then be reconstructed using known algorithms and displayed in two-dimensional or three-dimensional formats on a console monitor (not shown).

Figure 7A:
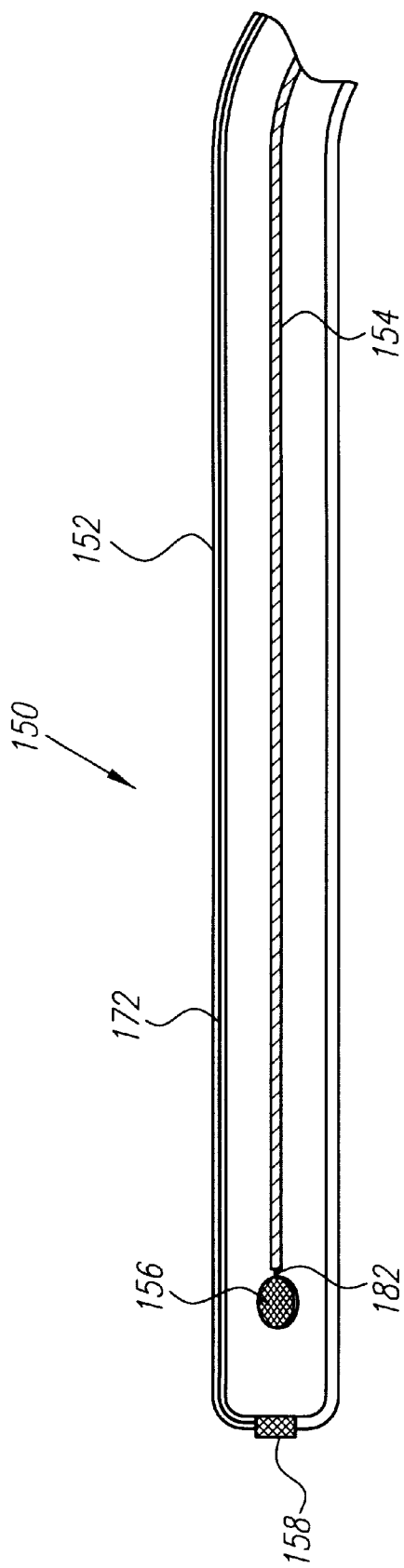
FIGS. 7A and 7B are cut-away, partial side views of a fourth preferred catheter assembly employing an embedded transmission line.
Figure 7B:
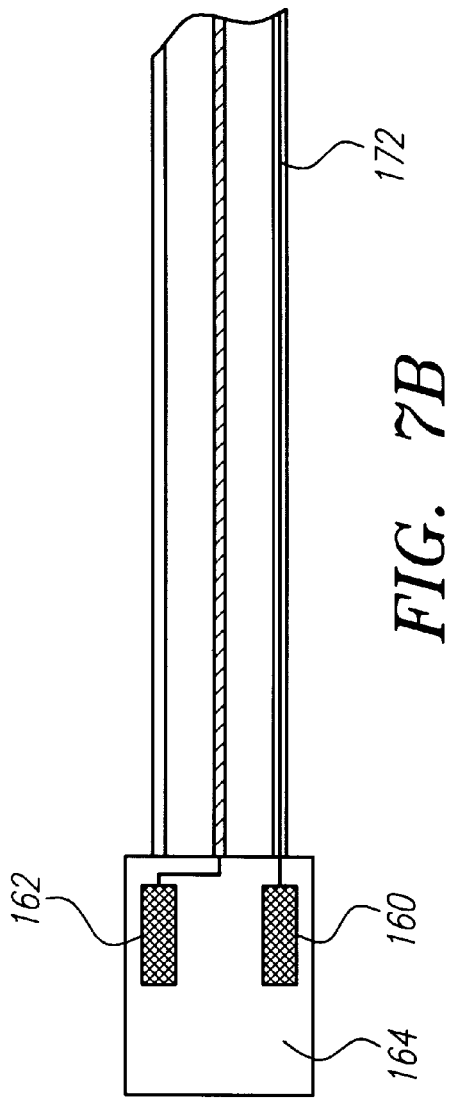
Figure 8:
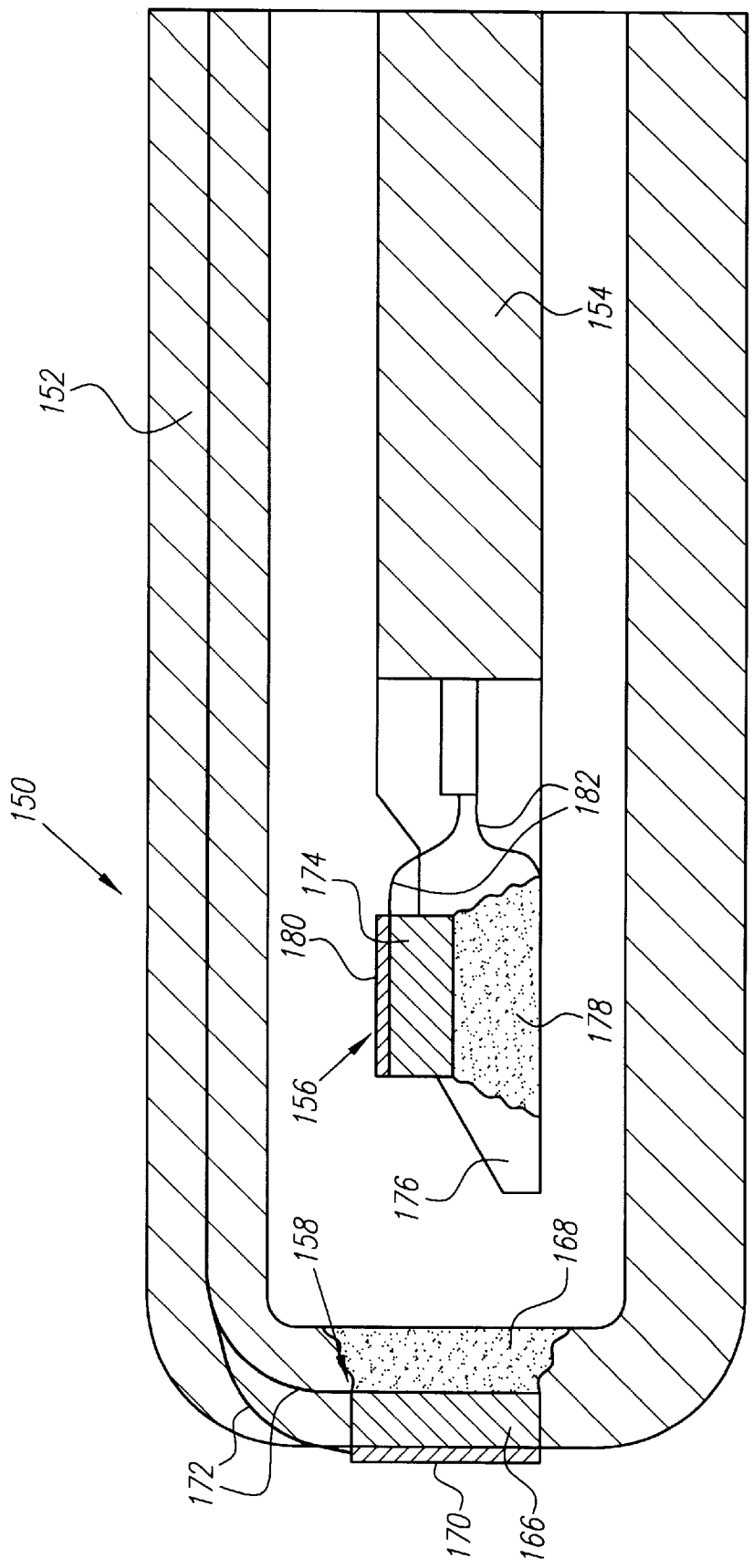
FIG. 8 is a cut-away, partial side view of the catheter assembly of FIGS. 7A and 7B.
Figure 10:
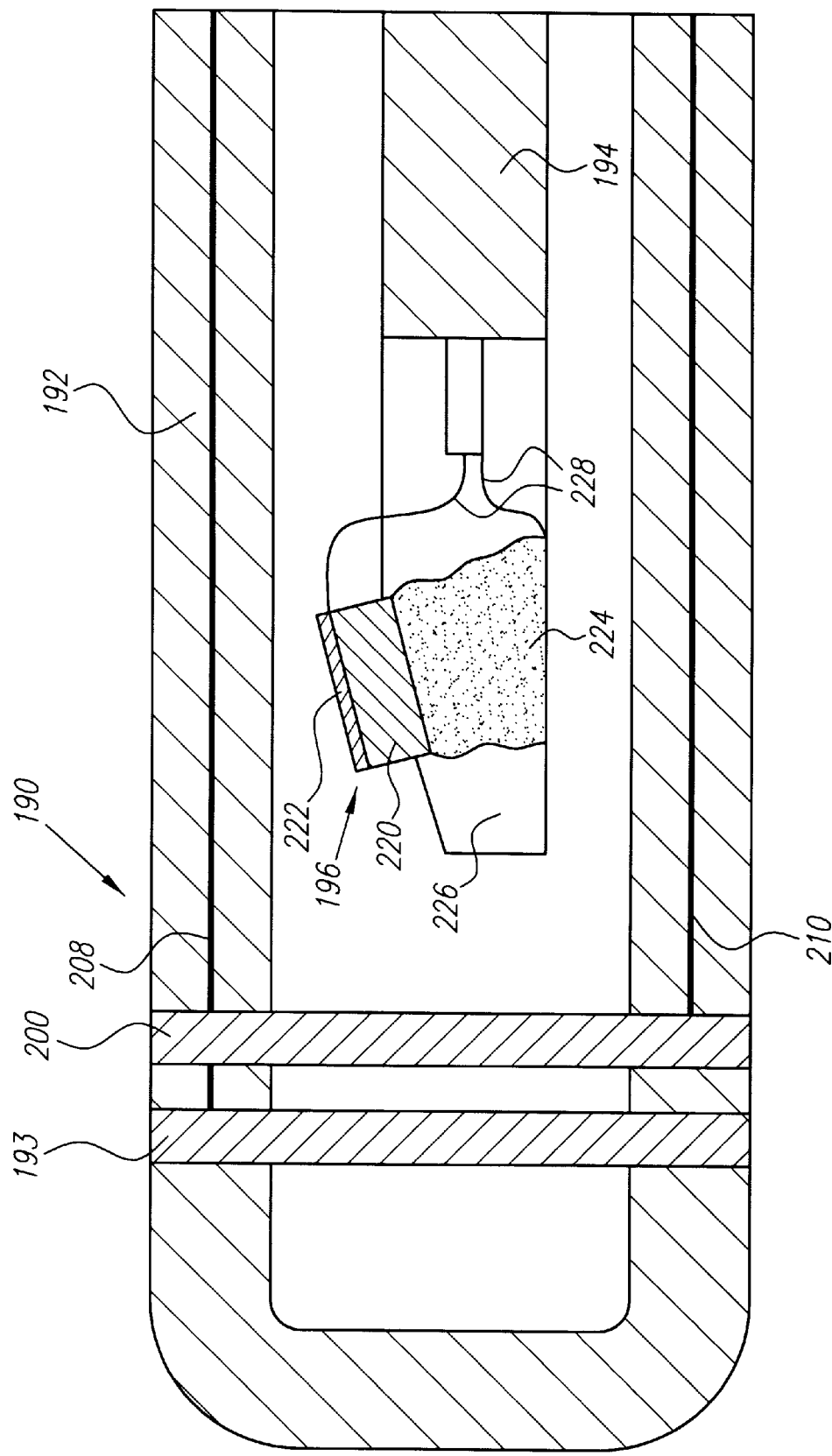
FIG. 10 is a cut-away, partial side view of the catheter assembly of FIGS. 9A and 9B.

Referring to FIGS. 7A, 7B, and 8, a fourth exemplary catheter assembly 150 is provided for measuring the velocity of the blood within a patient's vessel, while also providing ultrasonic imaging of the vessel wall. The catheter assembly 150 generally includes an elongate catheter body 152, a drive cable 154, a rotatable distal operative element 156, a non-rotatable distal operative element 158 and respective first and second non-rotatable proximal operative elements 160 and 162. The drive cable 154 is disposed through substantially the entire catheter body 152, both of which are mounted at the respective proximal ends thereof to a drive unit 164 proximal to the catheter assembly 150. Although the respective proximal operative elements 160 and 162 are shown as being disposed in the drive unit 164, the respective proximal operative elements 160 and 162 can be disposed external to the drive unit 164 without straying from the principles taught by this invention.

The non-rotatable distal operative element 158 comprises a first ultrasonic transducer element 166 (forward-looking transducer) for performing diagnostic functions such as Doppler measuring blood velocity. The first transducer element 166 is embedded in the distal tip of the catheter body 152, such that the face of the transducer element 166 is substantially perpendicular to the axis of the catheter body 152. A conductive transducer backing material 168 is potted beneath the first transducer element 166, and a transducer matching material 170 is bonded to the face of the transducer element 166 as a transducer matching layer 170 opposite the transducer backing material 168.

Alternatively, the non-rotatable distal operative element 158 comprises one or more ultrasonic transducer elements embedded in the catheter body 152, such that the face of the transducer element(s) are substantially parallel to the axis of the guide sheath. In this manner, the ultrasonic transducer elements can facilitate therapeutic functions, such as, e.g., micro-bubble encapsulated drug delivery. In this case, a concentrated ultrasound signal is provided to a diseased site in conjunction with the delivery of the micro-bubble encapsulated drugs, which are burst by the ultrasonic energy and released at the diseased site.

The first non-rotatable proximal element 160 comprises a first transceiver for alternately transmitting and receiving electrical signals to and from the first transducer element 166 to obtain data for Doppler measurements of the blood flow within the vessel in which the catheter assembly 150 is disposed. It can be appreciated, however, that the non-rotatable distal element 158 and the first non-rotatable proximal element 160 are not limited to a transducer element and transceiver, respectively, but can, without straying from the principles taught by this invention, respectively comprises any non-rotatable devices that are in electrical communications with one another.

The first transceiver 160 is electrically coupled to the first transducer element 166 through a first transmission line 172. The first transmission line 172 is preferably twisted pair, but can be any electrical conductor used in the manufacture of catheters, such as, e.g., coaxial cable. The first transmission line 172 is embedded within the wall of the catheter body 152 using an extrusion process. To provide a uniform impedance, it is essential during the extrusion process to minimize the presence of irregularities such as bubbles, and to keep constant the spacing of the transmission line within the catheter body 152. This results in a transmission line that is uniformly embedded within the catheter body 152 and having a uniform impedance through the length of the catheter body 152 for optimal signal transfer.

Preferably, the catheter body 152 forms a portion of the first transmission line 172. For example, as depicted in FIG. 13, the first transmission line 172 can be formed of two wires 173 with the catheter body 152 acting as the dielectric material between the wires 173. By using the equation, $z=[120/\operatorname{sqrt}(er)]*[\ln(2*s/d)]$, (where z=impedance, s=separation between the wire in inches, d=diameter of wire in inches, and er=effective relative dielectric constant of medium between the wires), the proper characteristic impedance of the transmission line 172 can be obtained. For instance, if the diameter (d) of the wires 173 is 0.010 inches, the separation (s) between the wires is 0.02 inches, and the effective relative dielectric constant (er) of the catheter body 152 is 2.7, then the impedance (z) of the transmission line 172 will be 100 ohms. Preferably, the wires 173 are insulated and twisted during extrusion, resulting in a uniform spacing of the twisted pair. It should be noted that twisting the wires is not required to achieve a uniform impedance, but is used to facilitate a uniform spacing of the wires.

The rotatable distal operative element 156 comprises a second ultrasonic transducer element 174 for performing ultrasonic imaging of the vessel wall. The second transducer element 174 is fixably mounted to a housing 176, such that the face of the second transducer element 174 is substantially parallel to the axis of the catheter body 152. In preferred embodiments, there is a slight angle between the face of the second transducer element 174 and the axis of the catheter assembly 150, thereby resulting in a "conical sweep" during imaging. A conductive transducer backing material 178 made of a suitable material is potted in the housing 176 and beneath the second transducer element 174, and a transducer matching material made of a suitable material is bonded to the face of the second transducer element 174 as a transducer matching layer 180 opposite the transducer backing material 178.

The second non-rotatable proximal element 162 comprises a second transceiver for alternately transmitting and receiving electrical signals to and from the second transducer element 174 to obtain data for imaging the walls of the vessel in which the catheter assembly 150 is disposed. It can be appreciated, however, that the rotatable distal operative element 156 and the second non-rotatable proximal operative element 162 are not limited to a transducer element and a transceiver, respectively, but can, without straying from the principles taught by this invention, respectively comprise any rotatable and non-rotatable device that are in electrical communication with each other.

The housing 176 and the drive cable 154 are mechanically and rotatable coupled to the drive unit 164, so that the drive unit 164 can rotate the drive cable 154 and the housing 176 as an integral unit. In particular, the proximal end of the drive cable 154 is suitably mounted to the drive unit 164 using means known in the art. The drive cable 154 is preferably designed in much the same manner as the drive cable 18 described with respect to the catheter assembly 10.

The second transceiver 162 is electrically coupled to the second transducer element 174 through a second transmission line 182. The second transmission line 182 is preferably coaxial cable, but can be any electrical conductor used in the manufacture of catheters, such as, e.g., twisted pair. The second transmission line 182 is disposed in the drive cable 154 using means known in the art.

The catheter assembly 150 performs ultrasonic imaging and/or Doppler measurements in much the same manner as that described with respect to the catheter assembly 60, with the exception that the first transmission line 172 eclipses the second transducer element 174, thereby slightly reducing the imaging capability of the catheter assembly 150.

Referring to FIGS. 9A, 9B, 10 and 11, a fifth exemplary catheter assembly 190 is provided for performing therapeutic applications such as ablation therapy, while also providing ultrasonic imaging of the vessel wall. The catheter assembly 190 generally includes an elongate catheter body 192, a drive cable 194, a rotatable distal operative element 196, respective first and second non-rotatable distal operative elements 198 and 200 and respective first and second non-rotatable proximal operative elements 202 and 204. The drive cable 194 is disposed through substantially the entire catheter body 192, both of which are mounted at the respective proximal ends thereof to a drive unit 206 proximal to the catheter assembly 190. Although the respective proximal operative elements 202 and 204 are shown as being disposed in the drive unit 206, the respective proximal operative elements 202 and 204 can be disposed external to the drive unit 206 without straying from the principles taught by this invention.

In particular, the first and second non-rotatable distal operative elements 198 and 200 respectively comprise ablation elements, such as, e.g., electrodes, for performing ablation therapy. A more detailed description of ablation electrodes is provided in Swanson et al., U.S. Pat. No. 5,582,609, which is fully incorporated herein by reference. First and second ablation elements 198 and 200 are fixed to the outer surface of the catheter body 192 by known methods, such as, e.g., mechanical interference. Alternatively, first and second ablation elements 198 and 200 may be any conductor used to establish electrical contact with a nonmetallic portion of a circuit, such as, e.g., conductive ink, the manufacture of which is described in copending application Ser. No. 08/879,343, filed Jun. 20, 1997, which is fully incorporated herein by reference. In alternative embodiments, the first and second non-rotatable distal operative elements 198 and 200 respectively comprise diagnostic elements, such as, e.g., mapping or pacing electrodes.

The first non-rotatable proximal element 202 comprises a source of energy for the respective first and second ablation elements 198 and 200. The source of energy may include, e.g., an RF energy generator such as those described in Jackson et al., U.S. Pat. No. 5,383,874 and Edwards et al., U.S. Pat. No. 5,456,682, which are fully incorporated herein by reference. It can be appreciated that the ablation elements 198 and 200 can be individually energized with two separate sources of energy without straying from the principles taught by this invention. It can also be appreciated that the respective non-rotatable distal elements 198 and 200 and the first non-rotatable proximal element 202 are not limited to ablation elements and a source of energy, respectively, but can, without straying from the principles taught by this invention, respectively comprise any non-rotatable devices that are in electrical communications with one another. For example, the non-rotatable distal elements 198 and 200 and the first non-rotatable proximal element 202 may respectively comprises mapping or pacing electrodes and a signal generator.

The RF generator 202 is electrically coupled to the ablation elements 198 and 200 through respective first and second transmission lines 208 and 210. Each of the respective transmission lines 208 and 210 preferably comprises a pair of lead wires, which are connected in parallel to the respective ablation elements 198 and 200. Various wire connection techniques are described in U.S. Pat. No. 5,582,609, which has previously been expressly incorporated herein by reference. The respective transmission lines 208 and 210 are embedded within the wall of the catheter body 192 using an extrusion process. It can be appreciated that the quantity of transmission lines that can be embedded in the catheter body 192 is not limited to two. For instance, FIG. 11 illustrates an alternative embodiment that employs four embedded transmission lines 212, 214, 216 and 218, which can be used to energize four ablation elements.

As with the catheter assembly 150, the rotatable distal operative element 196 comprises an ultrasonic transducer element 220 with opposing matching and backing layers 222 and 224, respectively. The transducer element 220 is mounted in a transducer housing 226, which is mechanically and rotatably coupled to the drive unit 206 via the drive cable 194. The second proximal non-rotatable operative element 204 comprises a transceiver, which is electrically coupled to the transducer element 220 via a transmission line 228 disposed in the drive cable 194.

In use, the catheter assembly 190 is intravascularly inserted into a patient and maneuvered by the physician until a desired region of the patient's coronary arteries is adjacent the transducer element 220. With the catheter assembly 190 properly positioned, ultrasonic imaging of the adjacent arterial tissue is performed to place the ablation elements next to abnormal tissue, such as, e.g., arythmic tissue. Arythmic tissue can be located using mapping catheters, with the ultrasonic imaging being used to identify the mapping catheter electrodes next to the abnormal tissue. The physician can then place the respective ablation elements 198 and 200 adjacent the identified mapping catheter electrodes, and thus the abnormal tissue. The RF generator 204 can then be operated to energize the respective ablation elements 198 and 200 via the respective transmission lines 208 and 210, thereby ablating the abnormal tissue. The respective transmission lines 208 and 210 eclipse the transducer element 220, thereby slightly reducing the imaging capability of the catheter assembly 190.

Figure 14B:
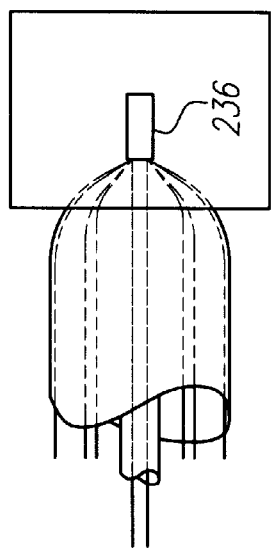
FIGS. 14A and 14B are cut-away, partial side views of a fifth preferred catheter assembly employing two embedded transmission lines.
Figure 14A:
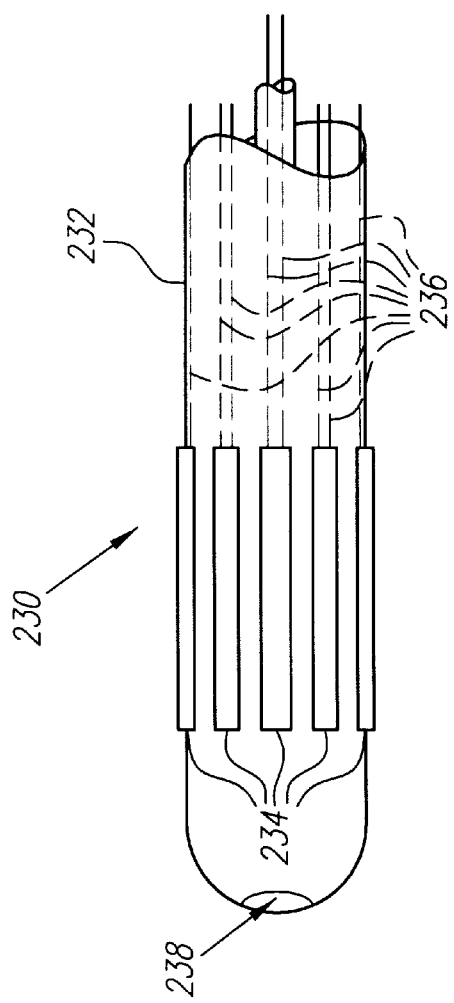

Referring to FIGS. 14A and 14B, a sixth exemplary catheter assembly 230 is provided for providing ultrasonic imaging of the vessel wall. The catheter assembly 230 generally includes an elongate catheter body 232, a plurality of distal operative elements 234 and a proximal operative element 236 coupled to the plurality of distal operative elements 234.

In particular, the plurality of distal operative elements 234 respectively comprise transducer elements embedded in the distal end of the catheter body 232 and circumferentially arranged therearound to form a phased array. For ease of illustration, a limited number of transducer elements are shown. A phased array is normally made up of many more transducer elements (typically 32 transducer elements). A more detailed description of the structure and utility of phased arrays is provided in Bom, U.S. Pat. No. 3,938,502, which is expressly and fully incorporated herein by reference.

The proximal operative element 236 comprises a transceiver, which is electrically coupled to the plurality of transducer elements 234 via respective transmission lines 236 (shown partially in phantom). The transceiver is configured to respectively provide a plurality of phased electrical signals to the respective transducer elements 232. The transmission lines 236 are embedded within the wall of the catheter body 232 using an extrusion process. The catheter body 232 includes a guide wire lumen 238 formed therethrough to provide over-the-wire guiding of the catheter body 232 to the imaging region.

Many of the features described with respect to the catheter assemblies 10, 60, 120, 150 and 190 can be variously combined to produce further embodiments. For example, ablation elements with corresponding transmission lines and an RF generator can be added to the respective catheter assemblies 10, 60, 120, 150, and 230 to provide ablation therapy capability. A forward looking transducer element can be added to the catheter assembly 190, either installed on the front of the housing 226 or embedded in the catheter body 192 to provide Doppler measurements of the blood flow. Catheter assemblies 150 and 190 can be manufactured exclusive of the rotatable transducer element to solely provide Doppler measurements of the blood flow or ablation therapy, respectively.

The number of transmission lines that can be embedded in the wall of the guide sheath, and thus the number of distal operative elements supported by a particular catheter assembly, is limited by space availability and impedance matching. In determining the characteristic impedance of the embedded transmission lines, the distance between the two wires, and the diameter of the wires of the transmission line must be taken into account. In general, the characteristic impedance of the transmission line is inversely proportional to the natural log of the distance between the two wires of the transmission line. Thus, the spacing between the respective wires for a given diameter of wires of embedded transmission lines should be chosen in a manner consistent with the desired impedance levels of the respective transmission lines.

What is claimed is:

1. A catheter assembly, comprising:
   an elongate catheter body having a proximal end and a distal end;
   a non-rotatable distal imaging element disposed on the distal portion of the elongate catheter body;
   a first conductor embedded substantially within the entire length of the catheter body, the first conductor having a distal end electrically coupled to the non-rotatable transducer element and a proximal end configured for electrically coupling to a first proximal operative element;
   a drive cable disposed in the catheter body, the drive cable having a proximal end and a distal end, and rotatable relative to the catheter body;
   a rotatable imaging element mounted to the distal end of the drive cable within the catheter body; and
   a second conductor disposed within the drive cable, the second conductor having a distal end electrically coupled to the rotatable imaging element and a proximal end configured for electrically coupling to a second proximal operative element.

2. The catheter assembly of claim 1, wherein the distal non-rotatable imaging element comprises a forward-looking ultrasonic transducer element mounted to the distal end of the catheter body.

3. The catheter assembly of claim 1, wherein the rotatable distal imaging element comprises a rotatable ultrasonic transducer element.

4. A catheter assembly, comprising:
   an elongate catheter body having a proximal end and a distal end;
   a plurality of non-rotatable distal imaging elements disposed on the elongate catheter body;
   a plurality of first conductors substantially embedded within the entire length of the catheter body, the plurality of first conductors having distal ends respectively electrically coupled to the plurality of non-rotatable distal imaging elements and proximal ends configured for respectively electrically coupling to at least one proximal operative element;
   a drive cable disposed in the catheter body, the drive cable having a proximal end and a distal end, and rotatable relative to the catheter body;
   a rotatable imaging element mounted to the distal end of the drive cable within the catheter body; and
   a second conductor disposed within the drive cable, the second conductor having a distal end electrically coupled to rotatable imaging element and a proximal end configured for electrically coupling to a proximal operative element.

5. The catheter assembly of claim 4, wherein the plurality of non-rotatable distal imaging elements comprise ablation elements mounted to the distal end of the catheter body.

6. The catheter assembly of claim 4, wherein the rotatable distal imaging element comprises a rotatable ultrasonic transducer element.

7. A catheter assembly, comprising:
   an elongate catheter body having a proximal end and a distal end;
   a distal imaging element disposed on the elongate catheter body;
   a first conductor embedded substantially within the entire length of the catheter body, the first conductor having a distal end electrically coupled to the distal imagine element and a proximal end configured for electrically coupling to a first proximal operative element;
   a drive cable disposed in the catheter body, the drive cable having a proximal end and a distal end, and rotatable relative to the catheter body;
   a rotatable distal imaging element mounted to the distal end of the drive cable within the catheter body; and
   a second conductor disposed within the drive cable, the second conductor having a distal end electrically coupled to rotatable imaging element and a proximal end configured for electrically coupling to a second proximal operative element.

8. The catheter assembly of claim 7, wherein the distal imaging element is non-rotatable.

9. The catheter assembly of claim 7, wherein the conductor is a transmission line.

10. The catheter assembly of claim 7, wherein the distal imaging element comprises a forward-looking ultrasonic transducer element mounted to the distal end of the catheter body.

11. The catheter assembly of claim 7, wherein the distal operative element comprises a forward-looking ultrasonic transducer element mounted to the distal end of the catheter body.

12. The catheter assembly of claim 7, wherein the rotatable distal imaging element comprises a rotatable ultrasonic transducer element.

13. A catheter assembly, comprising:

an elongate catheter body having a proximal end and a distal end;

a plurality of non-rotatable distal imaging elements disposed on the elongate catheter body;

a plurality of first conductors embedded substantially within the entire length of the catheter body, the plurality of first conductors having distal ends respectively electrically coupled to the plurality of non-rotatable distal imaging elements and proximal ends configured for respectively electrically coupling to at least one proximal operative element;

a drive cable disposed in the catheter body, the drive cable having a proximal end and a distal end, and rotatable relative to the catheter body;

a rotatable distal imaging element mounted to the distal end of the drive cable within the catheter body; and a second conductor disposed within the drive cable, the second conductor having a distal end electrically coupled to a rotatable imagine element and a proximal end configured for electrically coupling to a second proximal operative element.

14. The catheter assembly of claim 13, wherein the plurality of non-rotatable distal imaging elements comprise ablation elements mounted to the distal end of the catheter body.

15. The catheter assembly of claim 13, wherein the plurality of non-rotatable distal imaging elements respectively comprises a plurality of transducer elements circumferentially spaced around the elongate catheter body to form a phased array.

16. The catheter assembly of claim 13, wherein the rotatable distal operative element comprises a rotatable ultrasonic transducer element.

17. A catheter assembly, comprising:

an elongate catheter body having a proximal end and a distal end;

a distal imaging element disposed on the elongate catheter body;

a first pair of conductors embedded within the catheter body to form a transmission line having a characteristic impedance, the first pair of conductors having a distal end electrically coupled to the distal imaging element and a proximal end configured for electrically coupling to a first proximal operative element;

wherein a value of the characteristic impedance of the transmission line is selected by selecting a separation between the pair of conductors, a diameter of each of the pair of conductors, and an effective relative dielectric constant of the catheter body;

a drive cable disposed in the catheter body, the drive cable having a proximal end and a distal end, and rotatable relative to the catheter body;

a rotatable distal imaging element mounted to the distal end of the drive cable within the catheter body; and a second conductor disposed within the drive cable, the second conductor having a distal end electrically coupled to a rotatable imaging element and a proximal end configured for electrically coupling to a second proximal operative element.

18. The catheter assembly of claim 17, wherein the first conductor is embedded substantially within the entire length of the catheter body.

* * * * *

UNITED STATES PATENT AND TRADEMARK OFFICE
CERTIFICATE OF CORRECTION

PATENT NO.     : 6,245,020 B1
DATED          : June 12, 2001
INVENTOR(S)    : Thomas C. Moore et al.

It is certified that error appears in the above-identified patent and that said Letters Patent is hereby corrected as shown below:

<u>Title page,</u>
Item [75], Inventors, change the spelling of "Veijo Soursa" to -- Veijo Suorsa --.

<u>Column 2,</u>
Line 7, please change "lumen 308" to -- lumen 310 --.

<u>Column 8,</u>
Line 57, please change "48" to -- 42 --.

<u>Column 11,</u>
Line 44, please change "coupler 22" to -- coupler 14 --.

<u>Column 13,</u>
Line 49, after "transceivers" please insert -- 72 and 74 --.

<u>Column 15,</u>
Line 23, please change "360" to -- 360º -- .

<u>Column 18,</u>
Line 19, after "RF generator" please delete -- 202 --.
Line 58, please delete -- 204 --.

<u>Column 19,</u>
Line 18, after "operative element" please delete -- 236 --.
Line 20, please change "transducer elements 232" to -- transducer elements 234 --.

<u>Column 20,</u>
Line 54, please change "imagine" to -- imaging --.

UNITED STATES PATENT AND TRADEMARK OFFICE
CERTIFICATE OF CORRECTION

PATENT NO.    : 6,245,020 B1
DATED         : June 12, 2001
INVENTOR(S)   : Thomas C. Moore et al.

It is certified that error appears in the above-identified patent and that said Letters Patent is hereby corrected as shown below:

<u>Column 21,</u>
Line 36, please change "imagine" to -- imaging --.

Signed and Sealed this

Twentieth Day of August, 2002

Attest:

Attesting Officer

JAMES E. ROGAN
*Director of the United States Patent and Trademark Office*